United States Patent
Terao et al.

(10) Patent No.: US 11,427,828 B2
(45) Date of Patent: Aug. 30, 2022

(54) STABLE FC BINDING PROTEIN, METHOD FOR PRODUCING SAID PROTEIN, AND ANTIBODY ADSORBENT IN WHICH SAID PROTEIN IS USED

(71) Applicant: TOSOH CORPORATION, Yamaguchi (JP)

(72) Inventors: Yosuke Terao, Kanagawa (JP); Naoki Yamanaka, Kanagawa (JP); Natsuko Kizu, Kanagawa (JP); Satoshi Endo, Kanagawa (JP); Seigo Oe, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 303 days.

(21) Appl. No.: 16/606,486

(22) PCT Filed: Apr. 13, 2018

(86) PCT No.: PCT/JP2018/015487
§ 371 (c)(1),
(2) Date: Oct. 18, 2019

(87) PCT Pub. No.: WO2018/198817
PCT Pub. Date: Nov. 1, 2018

(65) Prior Publication Data
US 2020/0283779 A1    Sep. 10, 2020

(30) Foreign Application Priority Data
Apr. 26, 2017 (JP) .............................. JP2017-086808

(51) Int. Cl.
| | | |
|---|---|---|
| C07K 1/14 | (2006.01) |
| C07K 1/22 | (2006.01) |
| B01D 15/38 | (2006.01) |
| C07K 14/735 | (2006.01) |
| C07K 16/00 | (2006.01) |
| C12N 15/09 | (2006.01) |
| G01N 33/68 | (2006.01) |
| C12N 15/70 | (2006.01) |
| C07K 14/435 | (2006.01) |

(52) U.S. Cl.
CPC .............. *C12N 15/70* (2013.01); *C07K 1/14* (2013.01); *C07K 14/435* (2013.01); *C07K 2317/52* (2013.01)

(58) Field of Classification Search
None
See application file for complete search history.

(56) References Cited

U.S. PATENT DOCUMENTS

2008/0219947 A1   9/2008   Linette et al.
2017/0218044 A1   8/2017   Asaoka et al.

FOREIGN PATENT DOCUMENTS

| JP | 2017-118871 A | 7/2017 |
| JP | 2018-000174 A | 1/2018 |
| WO | WO 2010/048313 A2 | 4/2010 |
| WO | WO 2015/199154 A1 | 12/2015 |

OTHER PUBLICATIONS

Mccullum, E.O, et al. 2010 In: Braman J. (eds) In Vitro Mutagenesis Protocols. Methods in Molecular Biology (Methods and Protocols), vol. 634. Humana Press, Totowa, NJ: 103-109. (Year: 2010).*
Feng et al., "Design, Expression and Characterization of a Soluble Single-chain Functional Human Neonatal Fc Receptor" *Protein Expression and Purification* 79(1):66-71 (2011).
Andersen et al., "Ligand Binding and Antigenic Properties of a Human Neonatal Fc Receptor with Mutation of Two Unpaired Cysteine Residues" *FEBS Journal* 275(16):4097-4110 (2008).
Database: ID: B2MG_Human, AC: P61769, https://www.uniprot.org/uniprot/P61769.txt?version=155, UniProt [online], Nov. 30, 2016, 32 pages.
Raghavan et al., "Analysis of the pH Dependence of the Neonatal Fc Receptor/Immunoglobulin G Interaction Using Antibody and Receptor Variants," Biochemistry, 1995, 34:14649-14657.
Simister et al., "An Fc receptor structurally related to MHC class I antigens," Nature, 1989 337:184-187.
Takai, "Role of Fcγ receptors in immune regulation and diseases," Jpn. J. Clin. Immunol., 2005, 28(5):318-326.
ISR for PCT/JP2018/015487, dated Jul. 17, 2018.

* cited by examiner

*Primary Examiner* — Marsha Tsay
(74) *Attorney, Agent, or Firm* — Greenblum & Bernstein, P.L.C.

(57) ABSTRACT

The present invention addresses the problem of providing FcRn having improved stability with respect to heat and acids, a method for producing said FcRn, an antibody adsorbent in which said FcRn is used, and an antibody isolation method in which said adsorbent is used. The above problem is solved by substituting an amino acid residue at a specific position in an extracellular region of a human FcRn α chain and/or a β2 microglobulin region of a human FcRn β chain by another specific amino acid.

9 Claims, 1 Drawing Sheet
Specification includes a Sequence Listing.

SEQUENCE LISTING

```
<160> NUMBER OF SEQ ID NOS: 38

<210> SEQ ID NO 1
<211> LENGTH: 365
<212> TYPE: PRT
<213> ORGANISM: Homo sapiens
<220> FEATURE:
<223> OTHER INFORMATION: FcRn alpha unit

<400> SEQUENCE: 1

Met Gly Val Pro Arg Pro Gln Pro Trp Ala Leu Gly Leu Leu Leu Phe
1               5                   10                  15

Leu Leu Pro Gly Ser Leu Gly Ala Glu Ser His Leu Ser Leu Leu Tyr
            20                  25                  30

His Leu Thr Ala Val Ser Ser Pro Ala Pro Gly Thr Pro Ala Phe Trp
        35                  40                  45

Val Ser Gly Trp Leu Gly Pro Gln Gln Tyr Leu Ser Tyr Asn Ser Leu
    50                  55                  60

Arg Gly Glu Ala Glu Pro Cys Gly Ala Trp Val Trp Glu Asn Gln Val
65                  70                  75                  80
```

Ser Trp Tyr Trp Glu Lys Glu Thr Thr Asp Leu Arg Ile Lys Glu Lys
                85                  90                  95

Leu Phe Leu Glu Ala Phe Lys Ala Leu Gly Lys Gly Pro Tyr Thr
            100                 105                 110

Leu Gln Gly Leu Leu Gly Cys Glu Leu Gly Pro Asp Asn Thr Ser Val
        115                 120                 125

Pro Thr Ala Lys Phe Ala Leu Asn Gly Glu Glu Phe Met Asn Phe Asp
130                 135                 140

Leu Lys Gln Gly Thr Trp Gly Gly Asp Trp Pro Glu Ala Leu Ala Ile
145                 150                 155                 160

Ser Gln Arg Trp Gln Gln Gln Asp Lys Ala Ala Asn Lys Glu Leu Thr
                165                 170                 175

Phe Leu Leu Phe Ser Cys Pro His Arg Leu Arg Glu His Leu Glu Arg
            180                 185                 190

Gly Arg Gly Asn Leu Glu Trp Lys Glu Pro Pro Ser Met Arg Leu Lys
        195                 200                 205

Ala Arg Pro Ser Ser Pro Gly Phe Ser Val Leu Thr Cys Ser Ala Phe
        210                 215                 220

Ser Phe Tyr Pro Pro Glu Leu Gln Leu Arg Phe Leu Arg Asn Gly Leu
225                 230                 235                 240

Ala Ala Gly Thr Gly Gln Gly Asp Phe Gly Pro Asn Ser Asp Gly Ser
                245                 250                 255

Phe His Ala Ser Ser Ser Leu Thr Val Lys Ser Gly Asp Glu His His
            260                 265                 270

Tyr Cys Cys Ile Val Gln His Ala Gly Leu Ala Gln Pro Leu Arg Val
        275                 280                 285

Glu Leu Glu Ser Pro Ala Lys Ser Ser Val Leu Val Val Gly Ile Val
        290                 295                 300

Ile Gly Val Leu Leu Leu Thr Ala Ala Ala Val Gly Gly Ala Leu Leu
305                 310                 315                 320

Trp Arg Arg Met Arg Ser Gly Leu Pro Ala Pro Trp Ile Ser Leu Arg
                325                 330                 335

Gly Asp Asp Thr Gly Val Leu Leu Pro Thr Pro Gly Glu Ala Gln Asp
            340                 345                 350

Ala Asp Leu Lys Asp Val Asn Val Ile Pro Ala Thr Ala
        355                 360                 365

<210> SEQ ID NO 2
<211> LENGTH: 119
<212> TYPE: PRT
<213> ORGANISM: Homo sapiens
<220> FEATURE:
<223> OTHER INFORMATION: FcRn beta unit

<400> SEQUENCE: 2

Met Ser Arg Ser Val Ala Leu Ala Val Leu Ala Leu Leu Ser Leu Ser
1               5                   10                  15

Gly Leu Glu Ala Ile Gln Arg Thr Pro Lys Ile Gln Val Tyr Ser Arg
            20                  25                  30

His Pro Ala Glu Asn Gly Lys Ser Asn Phe Leu Asn Cys Tyr Val Ser
        35                  40                  45

Gly Phe His Pro Ser Asp Ile Glu Val Asp Leu Leu Lys Asn Gly Glu
    50                  55                  60

Arg Ile Glu Lys Val Glu His Ser Asp Leu Ser Phe Ser Lys Asp Trp
65                  70                  75                  80

```
Ser Phe Tyr Leu Leu Tyr Tyr Thr Glu Phe Thr Pro Thr Glu Lys Asp
                85                  90                  95

Glu Tyr Ala Cys Arg Val Asn His Val Thr Leu Ser Gln Pro Lys Ile
            100                 105                 110

Val Lys Trp Asp Arg Asp Met
        115

<210> SEQ ID NO 3
<211> LENGTH: 406
<212> TYPE: PRT
<213> ORGANISM: Artificial Sequence
<220> FEATURE:
<223> OTHER INFORMATION: b2mg+FcRn

<400> SEQUENCE: 3

Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Gly Ser Gly
            100                 105                 110

Gly Gly Gly Ser Gly Gly Gly Gly Ser Gly Gly Gly Gly Ser Ala Glu
        115                 120                 125

Ser His Leu Ser Leu Leu Tyr His Leu Thr Ala Val Ser Ser Pro Ala
    130                 135                 140

Pro Gly Thr Pro Ala Phe Trp Val Ser Gly Trp Leu Gly Pro Gln Gln
145                 150                 155                 160

Tyr Leu Ser Tyr Asn Ser Leu Arg Gly Glu Ala Glu Pro Cys Gly Ala
                165                 170                 175

Trp Val Trp Glu Asn Gln Val Ser Trp Tyr Trp Glu Lys Glu Thr Thr
            180                 185                 190

Asp Leu Arg Ile Lys Glu Lys Leu Phe Leu Glu Ala Phe Lys Ala Leu
        195                 200                 205

Gly Gly Lys Gly Pro Tyr Thr Leu Gln Gly Leu Leu Gly Cys Glu Leu
    210                 215                 220

Gly Pro Asp Asn Thr Ser Val Pro Thr Ala Lys Phe Ala Leu Asn Gly
225                 230                 235                 240

Glu Glu Phe Met Asn Phe Asp Leu Lys Gln Gly Thr Trp Gly Gly Asp
                245                 250                 255

Trp Pro Glu Ala Leu Ala Ile Ser Gln Arg Trp Gln Gln Asp Lys
            260                 265                 270

Ala Ala Asn Lys Glu Leu Thr Phe Leu Leu Phe Ser Cys Pro His Arg
        275                 280                 285

Leu Arg Glu His Leu Glu Arg Gly Arg Gly Asn Leu Glu Trp Lys Glu
    290                 295                 300

Pro Pro Ser Met Arg Leu Lys Ala Arg Pro Ser Ser Pro Gly Phe Ser
305                 310                 315                 320
```

Val Leu Thr Cys Ser Ala Phe Ser Phe Tyr Pro Pro Glu Leu Gln Leu
              325                 330                 335

Arg Phe Leu Arg Asn Gly Leu Ala Ala Gly Thr Gly Gln Gly Asp Phe
            340                 345                 350

Gly Pro Asn Ser Asp Gly Ser Phe His Ala Ser Ser Ser Leu Thr Val
              355                 360                 365

Lys Ser Gly Asp Glu His His Tyr Cys Cys Ile Val Gln His Ala Gly
          370                 375                 380

Leu Ala Gln Pro Leu Arg Val Glu Leu Glu Ser Pro Ala Lys Ser Ser
385                 390                 395                 400

His His His His His His
              405

<210> SEQ ID NO 4
<211> LENGTH: 1218
<212> TYPE: DNA
<213> ORGANISM: Artificial Sequence
<220> FEATURE:
<223> OTHER INFORMATION: b2mg+FcRn

<400> SEQUENCE: 4
atgggcattc aacgtacgcc aaaaatccaa gtttactctc gccatccggc agagaacggt      60
aagtctaact tcctgaattg ctacgtgtct ggtttccacc cgtccgacat cgaagttgac     120
ctcctcaaaa acggcgaacg tatcgaaaaa gttgagcact ctgacctcag cttcagcaag     180
gactggtcct tctacctgct ctactacacg gaattcaccc cgaccgagaa ggatgaatac     240
gcctgccgtg ttaatcacgt taccctgtct cagccgaaaa ttgtgaagtg ggaccgcgat     300
atgggtggtg gtggctctgg cggtggcggc tctggcggtg cggttccgg cggcggtggt      360 agcggtggcg gcggtagcgc ggaaagccat ctctccctgc tgtatcatct gactgcggtt     420
agctctccgg caccaggtac cccagccttc tgggtctctg gttggctggg tccgcagcaa     480
tacctctctt ataacagcct gcgcggtgaa gcagaaccat gcgtgcgtg gtttgggaa       540 aaccaggttt cttggtactg ggagaaagag acgaccgatc tgcgcatcaa ggaaaaactg     600
ttcctggaag ccttcaaagc gctgggcggt aaaggtccat atactctcca aggcctgctg     660
ggctgtgaac tcggtcctga caacacctct gttccgacgg ccaaattcgc actgaacggt     720
gaggagttta tgaattttga cctgaaacag ggcacctggg gtggcgattg gccagaggcg     780
ctcgctatct cccaacgctg gcagcagcaa gataaggcag cgaacaaaga actgacgttc     840
ctcctgtttt cttgcccgca ccgtctccgt gaacatctcg aacgtggtcg tggtaacctc     900
gaatggaagg agcctccgtc tatgcgtctg aaagcgcgtc cgtcttcccc gggttttct      960 gtactcactt gttccgcctt ctccttttac cctccagaac tccagctgcg cttcctgcgc    1020
aatggcctcg ctgcgggtac gggtcaggt gatttcggcc gaattctga cggctctttc       1080 cacgcgtctt ctagcctgac ggtgaaatct ggcgacgaac atcactactg ctgcatcgtg    1140
cagcacgcgg gtctcgcgca accgctccgc gttgagctcg aatccctgc caaatcttct     1200 catcatcatc atcatcat                                                   1218

<210> SEQ ID NO 5
<211> LENGTH: 406
<212> TYPE: PRT
<213> ORGANISM: Artificial Sequence
<220> FEATURE:
<223> OTHER INFORMATION: FcRn_m4

<400> SEQUENCE: 5

```
Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Gly Ser Gly
            100                 105                 110

Gly Gly Gly Ser Gly Gly Gly Ser Gly Gly Gly Gly Ser Ala Glu
        115                 120                 125

Ser His Leu Ser Leu Leu Tyr His Leu Thr Ala Val Ser Ser Pro Ala
    130                 135                 140

Pro Gly Thr Pro Ala Phe Trp Val Ser Gly Trp Leu Gly Pro Gln Gln
145                 150                 155                 160

Tyr Leu Ser Tyr Asn Ser Leu Arg Gly Glu Ala Glu Pro Arg Gly Ala
                165                 170                 175

Trp Val Trp Glu Asp Gln Val Ser Trp Tyr Trp Glu Lys Glu Thr Thr
            180                 185                 190

Asp Leu Arg Ile Lys Glu Lys Leu Phe Leu Glu Ala Phe Lys Ala Leu
        195                 200                 205

Gly Gly Lys Gly Pro Tyr Thr Leu Gln Gly Leu Leu Gly Cys Glu Leu
    210                 215                 220

Gly Pro Asp Asn Thr Ser Val Pro Thr Ala Lys Phe Ala Leu Asn Gly
225                 230                 235                 240

Glu Glu Phe Met Asn Phe Asp Leu Lys Gln Gly Thr Trp Gly Gly Asp
                245                 250                 255

Trp Pro Glu Ala Leu Ala Ile Ser Gln Arg Trp Gln Gln Asp Lys
            260                 265                 270

Ala Ala Asn Lys Glu Leu Thr Phe Leu Leu Phe Ser Cys Pro His Arg
        275                 280                 285

Leu Arg Glu His Leu Glu Leu Gly Arg Gly Asn Leu Glu Trp Lys Glu
    290                 295                 300

Pro Pro Ser Met Arg Leu Lys Ala Arg Pro Ser Ser Pro Gly Phe Ser
305                 310                 315                 320

Val Leu Thr Cys Ser Ala Phe Ser Phe Tyr Pro Pro Glu Leu Leu Leu
                325                 330                 335

Arg Phe Leu Arg Asn Gly Leu Ala Ala Gly Thr Gly Gln Gly Asp Phe
            340                 345                 350

Gly Pro Asn Ser Asp Gly Ser Phe His Ala Ser Ser Ser Leu Thr Val
        355                 360                 365

Lys Ser Gly Asp Glu His His Tyr Cys Cys Ile Val Gln His Ala Gly
    370                 375                 380

Leu Ala Gln Pro Leu Arg Val Glu Leu Glu Ser Pro Ala Lys Ser Ser
385                 390                 395                 400

His His His His His His
            405
```

<210> SEQ ID NO 6
<211> LENGTH: 406
<212> TYPE: PRT
<213> ORGANISM: Artificial Sequence
<220> FEATURE:
<223> OTHER INFORMATION: FcRn_m7

<400> SEQUENCE: 6

```
Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Gly Ser Gly
            100                 105                 110

Gly Gly Ser Gly Gly Gly Gly Ser Gly Gly Gly Ser Ala Glu
        115                 120                 125

Ser His Leu Ser Leu Leu Tyr His Leu Thr Ala Val Ser Ser Pro Ala
    130                 135                 140

Pro Gly Thr Pro Ala Phe Trp Val Ser Gly Trp Leu Gly Pro Gln Gln
145                 150                 155                 160

Tyr Leu Ser Tyr Asn Ser Leu Arg Gly Glu Ala Glu Pro Arg Gly Ala
                165                 170                 175

Trp Val Trp Glu Asp Gln Val Ser Trp Tyr Trp Glu Lys Glu Thr Thr
            180                 185                 190

Asp Leu Arg Ile Lys Glu Lys Leu Phe Leu Glu Ala Phe Lys Ala Leu
        195                 200                 205

Gly Gly Lys Gly Pro Tyr Thr Leu Gln Gly Leu Leu Gly Cys Glu Leu
    210                 215                 220

Gly Pro Asp Asn Thr Ser Val Pro Thr Ala Lys Phe Ala Leu Asn Gly
225                 230                 235                 240

Glu Glu Phe Met Asn Phe Asp Leu Lys Gln Gly Thr Trp Asp Gly Asp
                245                 250                 255

Trp Pro Glu Ala Leu Ala Ile Ser Gln Arg Trp Gln Gln Asp Lys
            260                 265                 270

Ala Ala Asn Lys Glu Leu Thr Phe Leu Leu Phe Ser Cys Pro His Arg
        275                 280                 285

Leu Arg Glu His Leu Glu Leu Gly Arg Gly Asp Leu Glu Trp Lys Glu
    290                 295                 300

Pro Pro Ser Met Arg Leu Lys Ala Arg Pro Ser Ser Pro Gly Phe Ser
305                 310                 315                 320

Val Leu Thr Cys Ser Ala Phe Ser Phe Tyr Pro Pro Glu Leu Leu Leu
                325                 330                 335

Arg Phe Leu Arg Asn Gly Leu Ala Ala Gly Thr Gly Gln Gly Asp Phe
            340                 345                 350

Gly Pro Asn Ser Asp Gly Ser Phe His Ala Ser Ser Leu Thr Val
        355                 360                 365
```

```
Lys Ser Gly Asp Glu His His Tyr Cys Cys Ile Val Gln His Ala Gly
        370             375             380

Leu Ala Gln Pro Leu Arg Val Glu Leu Glu Ser Pro Ala Glu Ser Ser
385             390             395             400

His His His His His His
            405

<210> SEQ ID NO 7
<211> LENGTH: 406
<212> TYPE: PRT
<213> ORGANISM: Artificial Sequence
<220> FEATURE:
<223> OTHER INFORMATION: FcRn_m8

<400> SEQUENCE: 7

Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Gly Ser Gly
            100                 105                 110

Gly Gly Gly Ser Gly Gly Gly Gly Ser Gly Gly Gly Gly Ser Ala Glu
            115                 120                 125

Ser His Leu Ser Leu Leu Tyr His Leu Thr Ala Val Ser Ser Pro Ala
    130                 135                 140

Pro Gly Thr Pro Ala Phe Trp Ala Ser Gly Trp Leu Gly Pro Gln Gln
145                 150                 155                 160

Tyr Leu Ser Tyr Asn Ser Leu Arg Gly Glu Ala Glu Pro Arg Gly Ala
                165                 170                 175

Trp Val Trp Glu Asp Gln Val Ser Trp Tyr Trp Glu Lys Glu Thr Thr
            180                 185                 190

Asp Leu Arg Ile Lys Glu Lys Leu Phe Leu Glu Ala Phe Lys Ala Leu
        195                 200                 205

Gly Gly Lys Gly Pro Tyr Thr Leu Gln Gly Leu Leu Gly Cys Glu Leu
210                 215                 220

Gly Pro Asp Asn Thr Ser Val Pro Thr Ala Lys Phe Ala Leu Asn Gly
225                 230                 235                 240

Glu Glu Phe Met Asn Phe Asp Leu Lys Gln Gly Thr Trp Asp Gly Asp
                245                 250                 255

Trp Pro Glu Ala Leu Ala Ile Ser Gln Arg Trp Gln Gln Asp Lys
            260                 265                 270

Ala Ala Asn Lys Glu Leu Thr Phe Leu Leu Phe Ser Cys Pro His Arg
        275                 280                 285

Leu Arg Glu His Leu Glu Leu Gly Arg Gly Asp Leu Glu Trp Lys Glu
    290                 295                 300

Pro Pro Ser Met Arg Leu Lys Ala Arg Pro Ser Ser Pro Gly Phe Ser
305                 310                 315                 320
```

```
Val Leu Thr Cys Ser Ala Phe Ser Phe Tyr Pro Pro Glu Leu Leu Leu
                325                 330                 335

Arg Phe Leu Arg Asn Gly Leu Ala Ala Gly Thr Gly Gln Gly Asp Phe
        340                 345                 350

Gly Pro Asn Ser Asp Gly Ser Phe His Ala Ser Ser Leu Thr Val
            355                 360                 365

Lys Ser Gly Asp Glu His His Tyr Cys Cys Ile Val Gln His Ala Gly
    370                 375                 380

Leu Ala Gln Pro Leu Arg Val Glu Leu Glu Ser Pro Ala Glu Ser Ser
385                 390                 395                 400

His His His His His His
            405

<210> SEQ ID NO 8
<211> LENGTH: 20
<212> TYPE: DNA
<213> ORGANISM: Artificial Sequence
<220> FEATURE:
<223> OTHER INFORMATION: primer F for T7Pro

<400> SEQUENCE: 8
taatacgact cactataggg                                             20

<210> SEQ ID NO 9
<211> LENGTH: 19
<212> TYPE: DNA
<213> ORGANISM: Artificial Sequence
<220> FEATURE:
<223> OTHER INFORMATION: primer R for T7Term

<400> SEQUENCE: 9
tatgctagtt attgctcag                                              19

<210> SEQ ID NO 10
<211> LENGTH: 437
<212> TYPE: PRT
<213> ORGANISM: Artificial Sequence
<220> FEATURE:
<223> OTHER INFORMATION: SP+FcRn+H6

<400> SEQUENCE: 10

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Ile Gln Arg Thr Pro Lys Ile Gln Val Tyr Ser Arg His Pro Ala
            35                  40                  45

Glu Asn Gly Lys Ser Asn Phe Leu Asn Cys Tyr Val Ser Gly Phe His
    50                  55                  60

Pro Ser Asp Ile Glu Val Asp Leu Leu Lys Asn Gly Glu Arg Ile Glu
65                  70                  75                  80

Lys Val Glu His Ser Asp Leu Ser Phe Ser Lys Asp Trp Ser Phe Tyr
                85                  90                  95

Leu Leu Tyr Tyr Thr Glu Phe Thr Pro Thr Glu Lys Asp Glu Tyr Ala
            100                 105                 110

Cys Arg Val Asn His Val Thr Leu Ser Gln Pro Lys Ile Val Lys Trp
    115                 120                 125

Asp Arg Asp Met Gly Gly Gly Gly Ser Gly Gly Gly Gly Ser Gly Gly
130                 135                 140
```

```
Gly Gly Ser Gly Gly Gly Ser Gly Gly Gly Ser Ala Glu Ser
145                 150                 155                 160

His Leu Ser Leu Leu Tyr His Leu Thr Ala Val Ser Pro Ala Pro
            165                 170                 175

Gly Thr Pro Ala Phe Trp Val Ser Gly Trp Leu Gly Pro Gln Gln Tyr
        180                 185                 190

Leu Ser Tyr Asn Ser Leu Arg Gly Glu Ala Glu Pro Cys Gly Ala Trp
            195                 200                 205

Val Trp Glu Asn Gln Val Ser Trp Tyr Trp Glu Lys Glu Thr Thr Asp
        210                 215                 220

Leu Arg Ile Lys Glu Lys Leu Phe Leu Glu Ala Phe Lys Ala Leu Gly
225                 230                 235                 240

Gly Lys Gly Pro Tyr Thr Leu Gln Gly Leu Leu Gly Cys Glu Leu Gly
                245                 250                 255

Pro Asp Asn Thr Ser Val Pro Thr Ala Lys Phe Ala Leu Asn Gly Glu
            260                 265                 270

Glu Phe Met Asn Phe Asp Leu Lys Gln Gly Thr Trp Gly Gly Asp Trp
        275                 280                 285

Pro Glu Ala Leu Ala Ile Ser Gln Arg Trp Gln Gln Gln Asp Lys Ala
            290                 295                 300

Ala Asn Lys Glu Leu Thr Phe Leu Leu Phe Ser Cys Pro His Arg Leu
305                 310                 315                 320

Arg Glu His Leu Glu Arg Gly Arg Gly Asn Leu Glu Trp Lys Glu Pro
                325                 330                 335

Pro Ser Met Arg Leu Lys Ala Arg Pro Ser Ser Pro Gly Phe Ser Val
            340                 345                 350

Leu Thr Cys Ser Ala Phe Ser Phe Tyr Pro Pro Glu Leu Gln Leu Arg
        355                 360                 365

Phe Leu Arg Asn Gly Leu Ala Ala Gly Thr Gly Gln Gly Asp Phe Gly
        370                 375                 380

Pro Asn Ser Asp Gly Ser Phe His Ala Ser Ser Ser Leu Thr Val Lys
385                 390                 395                 400

Ser Gly Asp Glu His His Tyr Cys Cys Ile Val Gln His Ala Gly Leu
                405                 410                 415

Ala Gln Pro Leu Arg Val Glu Leu Glu Ser Pro Ala Lys Ser Ser His
            420                 425                 430

His His His His His
        435

<210> SEQ ID NO 11
<211> LENGTH: 1314
<212> TYPE: DNA
<213> ORGANISM: Artificial Sequence
<220> FEATURE:
<223> OTHER INFORMATION: SP+FcRn+H6

<400> SEQUENCE: 11
atgaaaataa aaacaggtgc acgcatcctc gcattatccg cattaacgac gatgatgttt    60
tccgcctcgg ctctcgccaa aatcgaagaa gccatgggca ttcaacgtac gccaaaaatc   120
caagtttact ctcgccatcc ggcagagaac ggtaagtcta acttcctgaa ttgctacgtg   180
tctggtttcc acccgtccga catcgaagtt gacctcctca aaacggcga acgtatcgaa   240 aaagttgagc actctgacct cagcttcagc aaggactggt ccttctacct gctctactac   300
acggaattca ccccgaccga gaaggatgaa tacgcctgcc gtgttaatca cgttaccctg   360
```

```
tctcagccga aaattgtgaa gtgggaccgc gatatgggtg gtggtggctc tggcggtggc      420
ggctctggcg gtggcggttc cggcggcggt ggtagcggtg cggcggtag cgcggaaagc       480 catctctccc tgctgtatca tctgactgcg gttagctctc cggcaccagg taccccagcc      540
ttctgggtct ctggttggct gggtccgcag caatacctct cttataacag cctgcgcggt      600
gaagcagaac catgcggtgc gtgggtttgg gaaaaccagg tttcttggta ctgggagaaa      660
gagacgaccg atctgcgcat caaggaaaaa ctgttcctgg aagccttcaa agcgctgggc      720
ggtaaaggtc catatactct ccaaggcctg ctgggctgtg aactcggtcc tgacaacacc      780
tctgttccga cggccaaatt cgcactgaac ggtgaggagt ttatgaattt tgacctgaaa      840
cagggcacct ggggtggcga ttggccagag gcgctcgcta tctcccaacg ctggcagcag      900
caagataagg cagcgaacaa agaactgacg ttcctcctgt tttcttgccc gcaccgtctc      960
cgtgaacatc tcgaacgtgg tcgtggtaac ctcgaatgga aggagcctcc gtctatgcgt     1020
ctgaaagcgc gtccgtcttc cccgggtttt tctgtactca cttgttccgc cttctccttt     1080
taccctccag aactccagct gcgcttcctg cgcaatggcc tcgctgcggg tacgggtcag     1140
ggtgatttcg gcccgaattc tgacggctct ttccacgcgt cttctagcct gacggtgaaa     1200
tctggcgacg aacatcacta ctgctgcatc gtgcagcacg cgggtctcgc gcaaccgctc     1260
cgcgttgagc tcgaatcccc tgccaaatct tctcatcatc atcatcatca ttaa           1314
```

<210> SEQ ID NO 12
<211> LENGTH: 406
<212> TYPE: PRT
<213> ORGANISM: Artificial Sequence
<220> FEATURE:
<223> OTHER INFORMATION: FcRn_m1

<400> SEQUENCE: 12

```
Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Gly Ser Gly
            100                 105                 110

Gly Gly Gly Ser Gly Gly Gly Gly Ser Gly Gly Gly Ser Ala Glu
        115                 120                 125

Ser His Leu Ser Leu Leu Tyr His Leu Thr Ala Val Ser Ser Pro Ala
    130                 135                 140

Pro Gly Thr Pro Ala Phe Trp Val Ser Gly Trp Leu Gly Pro Gln Gln
145                 150                 155                 160

Tyr Leu Ser Tyr Asn Ser Leu Arg Gly Glu Ala Glu Pro Cys Gly Ala
                165                 170                 175

Trp Val Trp Glu Asp Gln Val Ser Trp Tyr Trp Glu Lys Glu Thr Thr
            180                 185                 190
```

```
Asp Leu Arg Ile Lys Glu Lys Leu Phe Leu Glu Ala Phe Lys Ala Leu
            195                 200                 205

Gly Gly Lys Gly Pro Tyr Thr Leu Gln Gly Leu Leu Gly Cys Glu Leu
    210                 215                 220

Gly Pro Asp Asn Thr Ser Val Pro Thr Ala Lys Phe Ala Leu Asn Gly
225                 230                 235                 240

Glu Glu Phe Met Asn Phe Asp Leu Lys Gln Gly Thr Trp Gly Gly Asp
                245                 250                 255

Trp Pro Glu Ala Leu Ala Ile Ser Gln Arg Trp Gln Gln Asp Lys
            260                 265                 270

Ala Ala Asn Lys Glu Leu Thr Phe Leu Leu Phe Ser Cys Pro His Arg
            275                 280                 285

Leu Arg Glu His Leu Glu Arg Gly Arg Gly Asn Leu Glu Trp Lys Glu
            290                 295                 300

Pro Pro Ser Met Arg Leu Lys Ala Arg Pro Ser Ser Pro Gly Phe Ser
305                 310                 315                 320

Val Leu Thr Cys Ser Ala Phe Ser Phe Tyr Pro Pro Glu Leu Gln Leu
                325                 330                 335

Arg Phe Leu Arg Asn Gly Leu Ala Ala Gly Thr Gly Gln Gly Asp Phe
            340                 345                 350

Gly Pro Asn Ser Asp Gly Ser Phe His Ala Ser Ser Ser Leu Thr Val
            355                 360                 365

Lys Ser Gly Asp Glu His His Tyr Cys Cys Ile Val Gln His Ala Gly
            370                 375                 380

Leu Ala Gln Pro Leu Arg Val Glu Leu Glu Ser Pro Ala Lys Ser Ser
385                 390                 395                 400

His His His His His His
            405

<210> SEQ ID NO 13
<211> LENGTH: 1218
<212> TYPE: DNA
<213> ORGANISM: Artificial Sequence
<220> FEATURE:
<223> OTHER INFORMATION: FcRn_m1

<400> SEQUENCE: 13
atgggcattc aacgtacgcc aaaaatccaa gtttactctc gccatccggc agagaacggt      60
aagtctaact tcctgaattg ctacgtgtct ggtttccacc cgtccgacat cgaagttgac     120
ctcctcaaaa acggcgaacg tatcgaaaaa gttgagcact ctgacctcag cttcagcaag     180
gactggtcct tctacctgct ctactacacg gaattcaccc cgaccgagaa ggatgaatac     240
gcctgccgtg ttaatcacgt tacccctgtct cagccgaaaa ttgtgaagtg ggaccgcgat     300
atgggtggtg gtggctctgg cggtggcggc tctggcggtg cggttccgg cggcggtggt      360 agcggtggcg gcgtagcgc ggaaagccat ctctccctgc tgtatcatct gactgcggtt     420
agctctccgg caccaggtac cccagccttc tgggtctctg gttggctggg tccgcagcaa     480
tacctctctt ataacagcct gcgcggtgaa gcagaaccat gcggtgcgtg ggtttgggaa     540
gaccaggttt cttggtactg ggagaaagag acgaccgatc tgcgcatcaa ggaaaaactg     600
ttcctggaag ccttcaaagc gctgggcggt aaaggtccat atactctcca aggcctgctg     660
ggctgtgaac tcggtcctga caacaccttct gttccgacgg ccaaattcgc actgaacggt     720
gaggagttta tgaattttga cctgaaacag ggcacctggg gtggcgattg gccagaggcg     780
ctcgctatct cccaacgctg gcagcagcaa gataaggcag cgaacaaaga actgacgttc     840
```

-continued

```
ctcctgtttt cttgcccgca ccgtctccgt gaacatctcg aacgtggtcg tggtaacctc        900
gaatggaagg agcctccgtc tatgcgtctg aaagcgcgtc cgtcttcccc gggttttctc       960
gtactcactt gttccgcctt ctccttttac cctccagaac tccagctgcg cttcctgcgc      1020
aatggcctcg ctgcgggtac gggtcagggt gatttcggcc cgaattctga cggctctttc      1080
cacgcgtctt ctagcctgac ggtgaaatct ggcgacgaac atcactactg ctgcatcgtg      1140
cagcacgcgg gtctcgcgca accgctccgc gttgagctcg aatcccctgc caaatcttct      1200
catcatcatc atcatcat                                                    1218
```

<210> SEQ ID NO 14
<211> LENGTH: 20
<212> TYPE: DNA
<213> ORGANISM: Artificial Sequence
<220> FEATURE:
<223> OTHER INFORMATION: primer R for m2

<400> SEQUENCE: 14
cacgcaccgc gtggttctgc         20

<210> SEQ ID NO 15
<211> LENGTH: 20
<212> TYPE: DNA
<213> ORGANISM: Artificial Sequence
<220> FEATURE:
<223> OTHER INFORMATION: primer F for m2

<400> SEQUENCE: 15
gcagaaccac gcggtgcgtg         20

<210> SEQ ID NO 16
<211> LENGTH: 406
<212> TYPE: PRT
<213> ORGANISM: Artificial Sequence
<220> FEATURE:
<223> OTHER INFORMATION: FcRn_m2

<400> SEQUENCE: 16

Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Ser Gly
            100                 105                 110

Gly Gly Gly Ser Gly Gly Gly Gly Ser Gly Gly Gly Ser Ala Glu
        115                 120                 125

Ser His Leu Ser Leu Leu Tyr His Leu Thr Ala Val Ser Ser Pro Ala
    130                 135                 140

Pro Gly Thr Pro Ala Phe Trp Val Ser Gly Trp Leu Gly Pro Gln Gln
145                 150                 155                 160

Tyr Leu Ser Tyr Asn Ser Leu Arg Gly Glu Ala Glu Pro Arg Gly Ala
            165                 170                 175

Trp Val Trp Glu Asp Gln Val Ser Trp Tyr Trp Glu Lys Glu Thr Thr
        180                 185                 190

Asp Leu Arg Ile Lys Glu Lys Leu Phe Leu Glu Ala Phe Lys Ala Leu
            195                 200                 205

Gly Gly Lys Gly Pro Tyr Thr Leu Gln Gly Leu Leu Gly Cys Glu Leu
        210                 215                 220

Gly Pro Asp Asn Thr Ser Val Pro Thr Ala Lys Phe Ala Leu Asn Gly
225                 230                 235                 240

Glu Glu Phe Met Asn Phe Asp Leu Lys Gln Gly Thr Trp Gly Gly Asp
            245                 250                 255

Trp Pro Glu Ala Leu Ala Ile Ser Gln Arg Trp Gln Gln Asp Lys
        260                 265                 270

Ala Ala Asn Lys Glu Leu Thr Phe Leu Leu Phe Ser Cys Pro His Arg
            275                 280                 285

Leu Arg Glu His Leu Glu Arg Gly Arg Gly Asn Leu Glu Trp Lys Glu
        290                 295                 300

Pro Pro Ser Met Arg Leu Lys Ala Arg Pro Ser Ser Pro Gly Phe Ser
305                 310                 315                 320

Val Leu Thr Cys Ser Ala Phe Ser Phe Tyr Pro Pro Glu Leu Gln Leu
            325                 330                 335

Arg Phe Leu Arg Asn Gly Leu Ala Ala Gly Thr Gly Gln Gly Asp Phe
        340                 345                 350

Gly Pro Asn Ser Asp Gly Ser Phe His Ala Ser Ser Leu Thr Val
            355                 360                 365

Lys Ser Gly Asp Glu His His Tyr Cys Cys Ile Val Gln His Ala Gly
    370                 375                 380

Leu Ala Gln Pro Leu Arg Val Glu Leu Glu Ser Pro Ala Lys Ser Ser
385                 390                 395                 400

His His His His His His
            405

<210> SEQ ID NO 17
<211> LENGTH: 1218
<212> TYPE: DNA
<213> ORGANISM: Artificial Sequence
<220> FEATURE:
<223> OTHER INFORMATION: FcRn_m2

<400> SEQUENCE: 17
atgggcattc aacgtacgcc aaaaatccaa gtttactctc gccatccggc agagaacggt    60
aagtctaact tcctgaattg ctacgtgtct ggtttccacc cgtccgacat cgaagttgac   120
ctcctcaaaa acggcgaacg tatcgaaaaa gttgagcact ctgacctcag cttcagcaag   180
gactggtcct ctacctgct ctactacacg gaattcaccc cgaccgagaa ggatgaatac   240
gcctgccgtg ttaatcacgt taccctgtct cagccgaaaa ttgtgaagtg ggaccgcgat   300
atgggtggtg gtggctctgg cggtggcggc tctggcggtg gcggttccgg cggcggtggt   360
agcggtggcg gcgtagcgc ggaaagccat ctctccctgc tgtatcatct gactgcggtt   420
agctctccgg caccaggtac cccagccttc tgggtctctg ttggctgggt ccgcagcaa   480 tacctctctt ataacagcct gcgcggtgaa gcagaaccac gcggtgcgtg ggtttgggaa   540
gaccaggttt cttggtactg ggagaaagag acgaccgatc tgcgcatcaa ggaaaaactg   600
ttcctggaag ccttcaaagc gctgggcggt aaaggtccat atactctcca aggcctgctg   660

```
ggctgtgaac tcggtcctga caacacctct gttccgacgg ccaaattcgc actgaacggt      720
gaggagttta tgaattttga cctgaaacag ggcacctggg gtggcgattg gccagaggcg      780
ctcgctatct cccaacgctg gcagcagcaa gataaggcag cgaacaaaga actgacgttc      840
ctcctgtttt cttgcccgca ccgtctccgt gaacatctcg aacgtggtcg tggtaacctc      900
gaatggaagg agcctccgtc tatgcgtctg aaagcgcgtc cgtcttcccc gggttttcct      960
gtactcactt gttccgcctt ctccttttac cctccagaac tccagctgcg cttcctgcgc     1020
aatggcctcg ctgcgggtac gggtcagggt gatttcggcc cgaattctga cggctctttc     1080
cacgcgtctt ctagcctgac ggtgaaatct ggcgacgaac atcactactg ctgcatcgtg     1140
cagcacgcgg gtctcgcgca accgctccgc gttgagctcg aatcccctgc caaatcttct     1200
catcatcatc atcatcat                                                   1218
```

<210> SEQ ID NO 18
<211> LENGTH: 22
<212> TYPE: DNA
<213> ORGANISM: Artificial Sequence
<220> FEATURE:
<223> OTHER INFORMATION: primer R for m3

<400> SEQUENCE: 18

```
cacgaccaag ttcgagatgt tc                                                22
```

<210> SEQ ID NO 19
<211> LENGTH: 22
<212> TYPE: DNA
<213> ORGANISM: Artificial Sequence
<220> FEATURE:
<223> OTHER INFORMATION: primer F for m3

<400> SEQUENCE: 19

```
gaacatctcg aacttggtcg tg                                                22
```

<210> SEQ ID NO 20
<211> LENGTH: 406
<212> TYPE: PRT
<213> ORGANISM: Artificial Sequence
<220> FEATURE:
<223> OTHER INFORMATION: FcRn_m3

<400> SEQUENCE: 20

Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Gly Ser Gly Gly Gly Gly Ser Gly
            100                 105                 110

Gly Gly Gly Ser Gly Gly Gly Gly Ser Gly Gly Gly Gly Ser Ala Glu
        115                 120                 125

```
Ser His Leu Ser Leu Leu Tyr His Leu Thr Ala Val Ser Ser Pro Ala
    130                 135                 140
Pro Gly Thr Pro Ala Phe Trp Val Ser Gly Trp Leu Gly Pro Gln Gln
145                 150                 155                 160
Tyr Leu Ser Tyr Asn Ser Leu Arg Gly Glu Ala Glu Pro Arg Gly Ala
                165                 170                 175
Trp Val Trp Glu Asp Gln Val Ser Trp Tyr Trp Glu Lys Glu Thr Thr
            180                 185                 190
Asp Leu Arg Ile Lys Glu Lys Leu Phe Leu Glu Ala Phe Lys Ala Leu
        195                 200                 205
Gly Gly Lys Gly Pro Tyr Thr Leu Gln Gly Leu Leu Gly Cys Glu Leu
    210                 215                 220
Gly Pro Asp Asn Thr Ser Val Pro Thr Ala Lys Phe Ala Leu Asn Gly
225                 230                 235                 240
Glu Glu Phe Met Asn Phe Asp Leu Lys Gln Gly Thr Trp Gly Gly Asp
                245                 250                 255
Trp Pro Glu Ala Leu Ala Ile Ser Gln Arg Trp Gln Gln Gln Asp Lys
            260                 265                 270
Ala Ala Asn Lys Glu Leu Thr Phe Leu Leu Phe Ser Cys Pro His Arg
        275                 280                 285
Leu Arg Glu His Leu Glu Leu Gly Arg Gly Asn Leu Glu Trp Lys Glu
    290                 295                 300
Pro Pro Ser Met Arg Leu Lys Ala Arg Pro Ser Ser Pro Gly Phe Ser
305                 310                 315                 320
Val Leu Thr Cys Ser Ala Phe Ser Phe Tyr Pro Pro Glu Leu Gln Leu
                325                 330                 335
Arg Phe Leu Arg Asn Gly Leu Ala Ala Gly Thr Gly Gln Gly Asp Phe
            340                 345                 350
Gly Pro Asn Ser Asp Gly Ser Phe His Ala Ser Ser Ser Leu Thr Val
        355                 360                 365
Lys Ser Gly Asp Glu His His Tyr Cys Cys Ile Val Gln His Ala Gly
    370                 375                 380
Leu Ala Gln Pro Leu Arg Val Glu Leu Glu Ser Pro Ala Lys Ser Ser
385                 390                 395                 400
His His His His His His
            405

<210> SEQ ID NO 21
<211> LENGTH: 1218
<212> TYPE: DNA
<213> ORGANISM: Artificial Sequence
<220> FEATURE:
<223> OTHER INFORMATION: FcRn_m3

<400> SEQUENCE: 21
atgggcattc aacgtacgcc aaaaatccaa gtttactctc gccatccggc agagaacggt    60
aagtctaact tcctgaattg ctacgtgtct ggtttccacc cgtccgacat cgaagttgac   120
ctcctcaaaa acggcgaacg tatcgaaaaa gttgagcact tgacctcag cttcagcaag    180 gactggtcct ctacctgct ctactacacg gaattcaccc cgaccgagaa ggatgaatac    240
gcctgccgtg ttaatcacgt taccctgtct cagccgaaaa ttgtgaagtg ggaccgcgat   300
atgggtggtg gtggctctgg cggtggcggc tctggcggtg cggttccgg cggcggtggt    360 agcggtggcg cggtagcgc ggaaagccat ctctccctgc tgtatcatct gactgcggtt   420
agctctccgg caccaggtac cccagccttc tgggtctctg gttggctggg tccgcagcaa   480
```

```
tacctctctt ataacagcct gcgcggtgaa gcagaaccac gcggtgcgtg ggtttgggaa      540
gaccaggttt cttggtactg ggagaaagag acgaccgatc tgcgcatcaa ggaaaaactg      600
ttcctggaag ccttcaaagc gctgggcggt aaaggtccat atactctcca aggcctgctg      660
ggctgtgaac tcggtcctga caacacctct gttccgacgg ccaaattcgc actgaacggt      720
gaggagttta tgaattttga cctgaaacag ggcacctggg gtggcgattg ccagaggcg      780 ctcgctatct cccaacgctg gcagcagcaa gataaggcag cgaacaaaga actgacgttc      840
ctcctgtttt cttgcccgca ccgtctccgt gaacatctcg aacttggtcg tggtaacctc      900
gaatggaagg agcctccgtc tatgcgtctg aaagcgcgtc cgtcttcccc gggttttct      960 gtactcactt gttccgcctt ctccttttac cctccagaac tccagctgcg cttcctgcgc     1020
aatggcctcg ctgcgggtac gggtcagggt gatttcggcc cgaattctga cggctctttc     1080
cacgcgtctt ctagcctgac ggtgaaatct ggcgacgaac atcactactg ctgcatcgtg     1140
cagcacgcgg gtctcgcgca accgctccgc gttgagctcg aatcccctgc caaatcttct     1200
catcatcatc atcatcat                                                   1218

<210> SEQ ID NO 22
<211> LENGTH: 21
<212> TYPE: DNA
<213> ORGANISM: Artificial Sequence
<220> FEATURE:
<223> OTHER INFORMATION: primer R for m4

<400> SEQUENCE: 22
gcgcagcagg agttctggag g                                                 21

<210> SEQ ID NO 23
<211> LENGTH: 21
<212> TYPE: DNA
<213> ORGANISM: Artificial Sequence
<220> FEATURE:
<223> OTHER INFORMATION: primer F for m4

<400> SEQUENCE: 23
cctccagaac tcctgctgcg c                                                 21

<210> SEQ ID NO 24
<211> LENGTH: 1218
<212> TYPE: DNA
<213> ORGANISM: Artificial Sequence
<220> FEATURE:
<223> OTHER INFORMATION: FcRn_m4

<400> SEQUENCE: 24
atgggcattc aacgtacgcc aaaaatccaa gtttactctc gccatccggc agagaacggt       60
aagtctaact tcctgaattg ctacgtgtct ggtttccacc cgtccgacat cgaagttgac      120
ctcctcaaaa acggcgaacg tatcgaaaaa gttgagcact ctgacctcag cttcagcaag      180
gactggtcct tctacctgct ctactacacg gaattcaccc cgaccgagaa ggatgaatac      240
gcctgccgtg ttaatcacgt taccctgtct cagccgaaaa ttgtgaagtg ggaccgcgat      300
atgggtggtg gtgcgctctg gcggtggcgg tctggcggtg gcggttccgg cggcggtggt      360
agcggtggcg gcggtagcgc ggaaagccat ctctcccctg ctgtatcatc tgactgcggt      420
agctctccgg caccaggtac cccagccttc tgggtctctg gttggctggg tccgcagcaa      480
tacctctctt ataacagcct gcgcggtgaa gcagaaccac gcggtgcgtg ggtttgggaa      540
```

```
gaccaggttt cttggtactg ggagaaagag acgaccgatc tgcgcatcaa ggaaaaactg    600
ttcctggaag ccttcaaagc gctgggcggt aaaggtccat atactctcca aggcctgctg    660
ggctgtgaac tcggtcctga caacacctct gttccgacgg ccaaattcgc actgaacggt    720
gaggagttta tgaattttga cctgaaacag ggcacctggg gtggcgattg ccagaggcg     780 ctcgctatct cccaacgctg gcagcagcaa gataaggcag cgaacaaaga actgacgttc    840
ctcctgtttt cttgcccgca ccgtctccgt gaacatctcg aacttggtcg tggtaacctc    900
gaatggaagg agcctccgtc tatgcgtctg aaagcgcgtc cgtcttcccc gggttttcct    960
gtactcactt gttccgcctt ctccttttac cctccagaac tcctgctgcg cttcctgcgc   1020
aatggcctcg ctgcgggtac gggtcagggt gatttcggcc cgaattctga cggctcttc    1080 cacgcgtctt ctagcctgac ggtgaaatct ggcgacgaac atcactactg ctgcatcgtg   1140
cagcacgcgg gtctcgcgca accgctccgc gttgagctcg aatcccctgc caaatcttct   1200
catcatcatc atcatcat                                                 1218
```

<210> SEQ ID NO 25
<211> LENGTH: 406
<212> TYPE: PRT
<213> ORGANISM: Artificial Sequence
<220> FEATURE:
<223> OTHER INFORMATION: FcRn_m5

<400> SEQUENCE: 25

Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Gly Ser Gly
            100                 105                 110

Gly Gly Ser Gly Gly Gly Gly Ser Gly Gly Gly Ser Ala Glu
        115                 120                 125

Ser His Leu Ser Leu Leu Tyr His Leu Thr Ala Val Ser Ser Pro Ala
    130                 135                 140

Pro Gly Thr Pro Ala Phe Trp Val Ser Gly Trp Leu Gly Pro Gln Gln
145                 150                 155                 160

Tyr Leu Ser Tyr Asn Ser Leu Arg Gly Glu Ala Glu Pro Arg Gly Ala
                165                 170                 175

Trp Val Trp Glu Asp Gln Val Ser Trp Tyr Trp Glu Lys Glu Thr Thr
            180                 185                 190

Asp Leu Arg Ile Lys Glu Lys Leu Phe Leu Glu Ala Phe Lys Ala Leu
        195                 200                 205

Gly Gly Lys Gly Pro Tyr Thr Leu Gln Gly Leu Leu Gly Cys Glu Leu
    210                 215                 220

Gly Pro Asp Asn Thr Ser Val Pro Thr Ala Lys Phe Ala Leu Asn Gly
225                 230                 235                 240

| | | | | | | | | | | | | |
|---|---|---|---|---|---|---|---|---|---|---|---|---|
|Glu|Glu|Phe|Met|Asn 245|Phe|Asp|Leu|Lys 250|Gln|Gly|Thr|Trp|Asp|Gly 255|Asp|

Trp Pro Glu Ala Leu Ala Ile Ser Gln Arg Trp Gln Gln Gln Asp Lys
          260                 265                 270

Ala Ala Asn Lys Glu Leu Thr Phe Leu Leu Phe Ser Cys Pro His Arg
          275                 280                 285

Leu Arg Glu His Leu Glu Leu Gly Arg Gly Asn Leu Glu Trp Lys Glu
  290                 295                 300

Pro Pro Ser Met Arg Leu Lys Ala Arg Pro Ser Ser Pro Gly Phe Ser
305                 310                 315                 320

Val Leu Thr Cys Ser Ala Phe Ser Phe Tyr Pro Pro Glu Leu Leu Leu
              325                 330                 335

Arg Phe Leu Arg Asn Gly Leu Ala Ala Gly Thr Gly Gln Gly Asp Phe
              340                 345                 350

Gly Pro Asn Ser Asp Gly Ser Phe His Ala Ser Ser Ser Leu Thr Val
              355                 360                 365

Lys Ser Gly Asp Glu His His Tyr Cys Cys Ile Val Gln His Ala Gly
          370                 375                 380

Leu Ala Gln Pro Leu Arg Val Glu Leu Glu Ser Pro Ala Lys Ser Ser
385                 390                 395                 400

His His His His His His
              405

<210> SEQ ID NO 26
<211> LENGTH: 1218
<212> TYPE: DNA
<213> ORGANISM: Artificial Sequence
<220> FEATURE:
<223> OTHER INFORMATION: FcRn_m5

<400> SEQUENCE: 26

```
atgggcattc aacgtacgcc aaaaatccaa gtttactctc gccatccggc agagaacggt    60
aagtctaact tcctgaattg ctacgtgtct ggtttccacc cgtccgacat cgaagttgac   120
ctcctcaaaa acggcgaacg tatcgaaaaa gttgagcact ctgacctcag cttcagcaag   180
gactggtcct ctacctgct ctactacacg gaattcaccc cgaccgagaa ggatgaatac   240
gcctgccgtg ttaatcacgt taccctgtct cagccgaaaa ttgtgaagtg ggaccgcgat   300
atgggtggtg gtgtggctctgg cggtggcggc tctggcggtg gcggttccgg cggcggtggt   360
agcggtggcg gcggtagcgc ggaaagccat ctctccctgc tgtatcatct gactgcggtt   420
agctctccgg caccaggtac cccagccttc tgggtctctg gttggctggg tccgcagcaa   480
tacctctctt ataacagcct gcgcggtgaa gcagaaccac gcggtgcgtg ggtttgggaa   540
gaccaggttt cttggtactg ggagaaagag acgaccgatc tgcgcatcaa ggaaaaactg   600
ttcctggaag ccttcaaagc gctggcggt aaaggtccat atactctcca aggcctgctg   660
ggctgtgaac tcgtcctga caacacctct gttccgacgg ccaaattcgc actgaacggt   720
gaggagttta tgaattttga cctgaaacag ggcacctggg atggcgattg gccagaggcg   780
ctcgctatct cccaacgctg gcagcagcaa gataaggcag cgaacaaaga actgacgttc   840
ctcctgtttt cttgcccgca ccgtctccgt gaacatctcg aacttggtcg tggtaacctc   900
gaatggaagg agcctccgtc tatgcgtctg aaagcgcgtc cgtcttcccc gggttttttct   960
gtactcactt gttccgcctt ctccttttac cctccagaac tcctgctgcg cttcctgcgc  1020
aatggcctcg ctgcgggtac gggtcagggt gatttcggcc cgaattctga cggctctttc  1080
```

```
cacgcgtctt ctagcctgac ggtgaaatct ggcgacgaac atcactactg ctgcatcgtg    1140
cagcacgcgg gtctcgcgca accgctccgc gttgagctcg aatcccctgc caaatcttct    1200
catcatcatc atcatcat                                                   1218
```

<210> SEQ ID NO 27
<211> LENGTH: 30
<212> TYPE: DNA
<213> ORGANISM: Artificial Sequence
<220> FEATURE:
<223> OTHER INFORMATION: primer R for m6

<400> SEQUENCE: 27

```
ccttccattc gaggtcacca cgaccaagtt                                        30
```

<210> SEQ ID NO 28
<211> LENGTH: 30
<212> TYPE: DNA
<213> ORGANISM: Artificial Sequence
<220> FEATURE:
<223> OTHER INFORMATION: primer F for m6

<400> SEQUENCE: 28

```
aacttggtcg tggtgacctc gaatggaagg                                        30
```

<210> SEQ ID NO 29
<211> LENGTH: 406
<212> TYPE: PRT
<213> ORGANISM: Artificial Sequence
<220> FEATURE:
<223> OTHER INFORMATION: FcRn_m6

<400> SEQUENCE: 29

Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Gly Ser Gly
            100                 105                 110

Gly Gly Gly Ser Gly Gly Gly Gly Ser Gly Gly Gly Gly Ser Ala Glu
        115                 120                 125

Ser His Leu Ser Leu Leu Tyr His Leu Thr Ala Val Ser Ser Pro Ala
    130                 135                 140

Pro Gly Thr Pro Ala Phe Trp Val Ser Gly Trp Leu Gly Pro Gln Gln
145                 150                 155                 160

Tyr Leu Ser Tyr Asn Ser Leu Arg Gly Glu Ala Glu Pro Arg Gly Ala
                165                 170                 175

Trp Val Trp Glu Asp Gln Val Ser Trp Tyr Trp Glu Lys Glu Thr Thr
            180                 185                 190

Asp Leu Arg Ile Lys Glu Lys Leu Phe Leu Glu Ala Phe Lys Ala Leu
        195                 200                 205

Gly Gly Lys Gly Pro Tyr Thr Leu Gln Gly Leu Gly Cys Glu Leu
    210                 215                 220

Gly Pro Asp Asn Thr Ser Val Pro Thr Ala Lys Phe Ala Leu Asn Gly
225                 230                 235                 240

Glu Glu Phe Met Asn Phe Asp Leu Lys Gln Gly Thr Trp Asp Gly Asp
                245                 250                 255

Trp Pro Glu Ala Leu Ala Ile Ser Gln Arg Trp Gln Gln Asp Lys
            260                 265                 270

Ala Ala Asn Lys Glu Leu Thr Phe Leu Leu Phe Ser Cys Pro His Arg
        275                 280                 285

Leu Arg Glu His Leu Glu Leu Gly Arg Gly Asp Leu Glu Trp Lys Glu
    290                 295                 300

Pro Pro Ser Met Arg Leu Lys Ala Arg Pro Ser Ser Pro Gly Phe Ser
305                 310                 315                 320

Val Leu Thr Cys Ser Ala Phe Ser Phe Tyr Pro Glu Leu Leu Leu
                325                 330                 335

Arg Phe Leu Arg Asn Gly Leu Ala Ala Gly Thr Gly Gln Gly Asp Phe
            340                 345                 350

Gly Pro Asn Ser Asp Gly Ser Phe His Ala Ser Ser Leu Thr Val
        355                 360                 365

Lys Ser Gly Asp Glu His His Tyr Cys Cys Ile Val Gln His Ala Gly
    370                 375                 380

Leu Ala Gln Pro Leu Arg Val Glu Leu Glu Ser Pro Ala Lys Ser Ser
385                 390                 395                 400

His His His His His His
            405

<210> SEQ ID NO 30
<211> LENGTH: 1218
<212> TYPE: DNA
<213> ORGANISM: Artificial Sequence
<220> FEATURE:
<223> OTHER INFORMATION: FcRn_m6

<400> SEQUENCE: 30
atgggcattc aacgtacgcc aaaaatccaa gttactctc gccatccggc agagaacggt      60
aagtctaact tcctgaattg ctacgtgtct ggtttccacc cgtccgacat cgaagttgac    120
ctcctcaaaa acggcgaacg tatcgaaaaa gttgagcact tgacctcag cttcagcaag    180 gactggtcct tctacctgct ctactacacg gaattcaccc cgaccgagaa ggatgaatac    240
gcctgccgtg ttaatcacgt taccctgtct cagccgaaaa ttgtgaagtg ggaccgcgat    300
atgggtggtg gtggctctgg cggtggcggc tctggcggtg cgggttccgg cggcggtggt    360
agcggtggcg gcgtagcgc ggaaagccat ctctccctgc tgtatcatct gactgcggtt    420
agctctccgg caccaggtac cccagccttc tgggtctctg gttggctggg tccgcagcaa    480
tacctctctt ataacagcct gcgcggtgaa gcagaaccac gcggtgcgtg ggtttgggaa    540
gaccaggttt cttggtactg ggagaaagag acgaccgatc tgcgcatcaa ggaaaaactg    600
ttcctggaag ccttcaaagc gctgggcggt aaaggtccat atactctcca aggcctgctg    660
ggctgtgaac tcggtcctga caacacctct gttccgacgg ccaaattcgc actgaacggt    720
gaggagttta tgaattttga cctgaaacag ggcacctggg atggcgattg gccagaggcg    780
ctcgctatct cccaacgctg gcagcagcaa gataaggcag cgaacaaaga actgacgttc    840
ctcctgtttt cttgcccgca ccgtctccgt gaacatctcg aacttggtcg tggtgacctc    900

```
gaatggaagg agcctccgtc tatgcgtctg aaagcgcgtc cgtcttcccc gggttttttct      960 gtactcactt gttccgcctt ctccttttac cctccagaac tcctgctgcg cttcctgcgc     1020
aatggcctcg ctgcgggtac gggtcagggt gatttcggcc cgaattctga cggctctttc     1080
cacgcgtctt ctagcctgac ggtgaaatct ggcgacgaac atcactactg ctgcatcgtg     1140
cagcacgcgg gtctcgcgca accgctccgc gttgagctcg aatcccctgc caaatcttct     1200
catcatcatc atcatcat                                                    1218
```

<210> SEQ ID NO 31
<211> LENGTH: 23
<212> TYPE: DNA
<213> ORGANISM: Artificial Sequence
<220> FEATURE:
<223> OTHER INFORMATION: primer R for m7

<400> SEQUENCE: 31

```
atgagaagat tcggcagggg att                                                23
```

<210> SEQ ID NO 32
<211> LENGTH: 23
<212> TYPE: DNA
<213> ORGANISM: Artificial Sequence
<220> FEATURE:
<223> OTHER INFORMATION: primer F for m7

<400> SEQUENCE: 32

```
aatcccctgc cgaatcttct cat                                                23
```

<210> SEQ ID NO 33
<211> LENGTH: 1218
<212> TYPE: DNA
<213> ORGANISM: Artificial Sequence
<220> FEATURE:
<223> OTHER INFORMATION: FcRn_m7

<400> SEQUENCE: 33

```
atgggcattc aacgtacgcc aaaaatccaa gtttactctc gccatccggc agagaacggt        60
aagtctaact tcctgaattg ctacgtgtct ggtttccacc cgtccgacat cgaagttgac       120
ctcctcaaaa acggcgaacg tatcgaaaaa gttgagcact ctgacctcag cttcagcaag       180
gactggtcct tctacctgct ctactacacg gaattcaccc cgaccgagaa ggatgaatac       240
gcctgccgtg ttaatcacgt taccctgtct cagccgaaaa ttgtgaagtg ggaccgcgat       300
atgggtggtg gtggctctgg cggtggcggc tctggcggtg gcggttccgg cggcggtggt       360
agcggtggcg gcggtagcgc ggaaagccat ctctccctgc tgtatcatct gactgcggtt       420
agctctccgg caccaggtac cccagccttc tgggtctctg gttggctggg tccgcagcaa       480
tacctctctt ataacagcct gcgcggtgaa gcagaaccac gcggtgcgtg ggtttgggaa       540
gaccaggttt cttggtactg ggagaaagag acgaccgatc tgcgcatcaa ggaaaaactg       600
ttcctggaag ccttcaaagc gctgggcggt aaaggtccat atactctcca aggcctgctg       660
ggctgtgaac tcggtcctga caacacctct gttccgacgg ccaaattcgc actgaacggt       720
gaggagttta tgaattttga cctgaaacag ggcacctggg atggcgattg ccagaggcg        780 ctcgctatct cccaacgctg gcagcagcaa gataaggcag cgaacaaaga actgacgttc       840
ctcctgtttt cttgcccgca ccgtctccgt gaacatctcg aacttggtcg tggtgacctc       900
gaatggaagg agcctccgtc tatgcgtctg aaagcgcgtc cgtcttcccc gggtttttct      960
gtactcactt gttccgcctt ctccttttac cctccagaac tcctgctgcg cttcctgcgc     1020
```

```
aatggcctcg ctgcgggtac gggtcagggt gatttcggcc cgaattctga cggctctttc    1080
cacgcgtctt ctagcctgac ggtgaaatct ggcgacgaac atcactactg ctgcatcgtg    1140
cagcacgcgg gtctcgcgca accgctccgc gttgagctcg aatcccctgc cgaatcttct    1200
catcatcatc atcatcat                                                  1218

<210> SEQ ID NO 34
<211> LENGTH: 1218
<212> TYPE: DNA
<213> ORGANISM: Artificial Sequence
<220> FEATURE:
<223> OTHER INFORMATION: FcRn_m8

<400> SEQUENCE: 34
atgggcattc aacgtacgcc aaaaatccaa gtttactctc gccatccggc agagaacggt     60
aagtctaact tcctgaattg ctacgtgtct ggtttccacc cgtccgacat cgaagttgac    120
ctcctcaaaa acggcgaacg tatcgaaaaa gttgagcact ctgacctcag cttcagcaag    180
gactggtcct tctacctgct ctactacacg gaattcaccc cgaccgagaa ggatgaatac    240
gcctgccgtg ttaatcacgt taccctgtct cagccgaaaa ttgtgaagtg ggaccgcgat    300
atgggtggtg gtggctctgg cggtggcggc tctggcggtg gcggttccgg cggcggtggt    360
agcggtggcg gcggtagcgc ggaaaagcca t ctctccctgc tgtatcatct gactgcggtt    420
agctctccgg caccaggtac cccagccttc tgggcctctg gttggctggg tccgcagcaa    480
tacctctctt ataacagcct gcgcggtgaa gcagaaccac gcggtgcgtg ggtttgggaa    540
gaccaggttt cttggtactg ggagaaagag acgaccgatc tgcgcatcaa ggaaaaactg    600
ttcctggaag ccttcaaagc gctgggcggt aaaggtccat atactctcca aggcctgctg    660
ggctgtgaac tcggtcctga caacacctct gttccgacgg ccaaattcgc actgaacggt    720
gaggagttta tgaattttga cctgaaacag ggcacctggg atggcgattg ccagaggcg     780 ctcgctatct cccaacgctg gcagcagcaa gataaggcag cgaacaaaga actgacgttc    840
ctcctgtttt cttgcccgca ccgtctccgt gaacatctcg aacttggtcg tggtgacctc    900
gaatggaagg agcctccgtc tatgcgtctg aaagcgcgtc cgtcttcccc gggtttttct    960
gtactcactt gttccgcctt ctccttttac cctccagaac tcctgctgcg cttcctgcgc   1020
aatggcctcg ctgcgggtac gggtcagggt gatttcggcc cgaattctga cggctctttc   1080
cacgcgtctt ctagcctgac ggtgaaatct ggcgacgaac atcactactg ctgcatcgtg   1140
cagcacgcgg gtctcgcgca accgctccgc gttgagctcg aatcccctgc cgaatcttct   1200
catcatcatc atcatcat                                                 1218

<210> SEQ ID NO 35
<211> LENGTH: 59
<212> TYPE: DNA
<213> ORGANISM: Artificial Sequence
<220> FEATURE:
<223> OTHER INFORMATION: primer R for Cys

<400> SEQUENCE: 35
cccaagctta tccgcaggta tcgttgcggc acccagaaga ttcggcaggg gattcgagc     59

<210> SEQ ID NO 36
<211> LENGTH: 408
<212> TYPE: PRT
<213> ORGANISM: Artificial Sequence
<220> FEATURE:
```

<223> OTHER INFORMATION: FcRn_m7Cys

<400> SEQUENCE: 36

Met Gly Ile Gln Arg Thr Pro Lys Ile Gln Val Tyr Ser Arg His Pro
1               5                   10                  15

Ala Glu Asn Gly Lys Ser Asn Phe Leu Asn Cys Tyr Val Ser Gly Phe
            20                  25                  30

His Pro Ser Asp Ile Glu Val Asp Leu Leu Lys Asn Gly Glu Arg Ile
        35                  40                  45

Glu Lys Val Glu His Ser Asp Leu Ser Phe Ser Lys Asp Trp Ser Phe
    50                  55                  60

Tyr Leu Leu Tyr Tyr Thr Glu Phe Thr Pro Thr Glu Lys Asp Glu Tyr
65                  70                  75                  80

Ala Cys Arg Val Asn His Val Thr Leu Ser Gln Pro Lys Ile Val Lys
                85                  90                  95

Trp Asp Arg Asp Met Gly Gly Gly Ser Gly Gly Gly Gly Ser Gly
            100                 105                 110

Gly Gly Gly Ser Gly Gly Gly Gly Ser Gly Gly Gly Gly Ser Ala Glu
            115                 120                 125

Ser His Leu Ser Leu Leu Tyr His Leu Thr Ala Val Ser Ser Pro Ala
    130                 135                 140

Pro Gly Thr Pro Ala Phe Trp Val Ser Gly Trp Leu Gly Pro Gln Gln
145                 150                 155                 160

Tyr Leu Ser Tyr Asn Ser Leu Arg Gly Glu Ala Glu Pro Arg Gly Ala
                165                 170                 175

Trp Val Trp Glu Asp Gln Val Ser Trp Tyr Trp Glu Lys Glu Thr Thr
            180                 185                 190

Asp Leu Arg Ile Lys Glu Lys Leu Phe Leu Glu Ala Phe Lys Ala Leu
        195                 200                 205

Gly Gly Lys Gly Pro Tyr Thr Leu Gln Gly Leu Leu Gly Cys Glu Leu
210                 215                 220

Gly Pro Asp Asn Thr Ser Val Pro Thr Ala Lys Phe Ala Leu Asn Gly
225                 230                 235                 240

Glu Glu Phe Met Asn Phe Asp Leu Lys Gln Gly Thr Trp Asp Gly Asp
                245                 250                 255

Trp Pro Glu Ala Leu Ala Ile Ser Gln Arg Trp Gln Gln Asp Lys
            260                 265                 270

Ala Ala Asn Lys Glu Leu Thr Phe Leu Leu Phe Ser Cys Pro His Arg
        275                 280                 285

Leu Arg Glu His Leu Glu Leu Gly Arg Gly Asp Leu Glu Trp Lys Glu
    290                 295                 300

Pro Pro Ser Met Arg Leu Lys Ala Arg Pro Ser Ser Pro Gly Phe Ser
305                 310                 315                 320

Val Leu Thr Cys Ser Ala Phe Ser Phe Tyr Pro Pro Glu Leu Leu Leu
                325                 330                 335

Arg Phe Leu Arg Asn Gly Leu Ala Ala Gly Thr Gly Gln Gly Asp Phe
            340                 345                 350

Gly Pro Asn Ser Asp Gly Ser Phe His Ala Ser Ser Ser Leu Thr Val
        355                 360                 365

Lys Ser Gly Asp Glu His His Tyr Cys Cys Ile Val Gln His Ala Gly
    370                 375                 380

Leu Ala Gln Pro Leu Arg Val Glu Leu Glu Ser Pro Ala Glu Ser Ser
385                 390                 395                 400

Gly Cys Arg Asn Asp Thr Cys Gly
             405

<210> SEQ ID NO 37
<211> LENGTH: 1227
<212> TYPE: DNA
<213> ORGANISM: Artificial Sequence
<220> FEATURE:
<223> OTHER INFORMATION: FcRn_m7Cys

<400> SEQUENCE: 37
atgggcattc aacgtacgcc aaaaatccaa gtttactctc gccatccggc agagaacggt    60
aagtctaact tcctgaattg ctacgtgtct ggtttccacc cgtccgacat cgaagttgac   120
ctcctcaaaa acggcgaacg tatcgaaaaa gttgagcact ctgacctcag cttcagcaag   180
gactggtcct tctacctgct ctactacacg gaattcaccc cgaccgagaa ggatgaatac   240
gcctgccgtg ttaatcacgt taccctgtct cagccgaaaa ttgtgaagtg ggaccgcgat   300
atgggtggtg gtggctctgg cggtggcggc tctggcggtg gcggttccgg cggcggtggt   360
agcggtggcg gcggtagcgc ggaaagccat ctctccctgc tgtatcatct gactgcggtt   420
agctctccgg caccaggtac cccagccttc tgggtctctg gttggctggg tccgcagcaa   480
tacctctctt ataacagcct gcgcggtgaa gcagaaccac gcggtgcgtg ggtttgggaa   540
gaccaggttt cttggtactg ggagaaagag acgaccgatc tgcgcatcaa ggaaaaactg   600
ttcctggaag ccttcaaagc gctgggcggt aaaggtccat atactctcca aggcctgctg   660
ggctgtgaac tcggtcctga caacacctct gttccgacgg ccaaattcgc actgaacggt   720
gaggagttta tgaattttga cctgaaacag ggcacctggg atggcgattg ccagaggcg   780 ctcgctatct cccaacgctg gcagcagcaa gataaggcag cgaacaaaga actgacgttc   840
ctcctgtttt cttgcccgca ccgtctccgt gaacatctcg aacttggtcg tggtgacctc   900
gaatggaagg agcctccgtc tatgcgtctg aaagcgcgtc cgtcttcccc gggttttct   960 gtactcactt gttccgcctt ctcctttac cctccagaac tcctgctgcg cttcctgcgc  1020
aatggcctcg ctgcgggtac gggtcagggt gatttcggcc cgaattctga cggctctttc  1080
cacgcgtctt ctagcctgac ggtgaaatct ggcgacgaac atcactactg ctgcatcgtg  1140
cagcacgcgg gtctcgcgca accgctccgc gttgagctcg aatcccctgc cgaatcttct  1200
gggtgccgca acgatacctg cggataa                                     1227

<210> SEQ ID NO 38
<211> LENGTH: 4
<212> TYPE: PRT
<213> ORGANISM: Artificial Sequence
<220> FEATURE:
<223> OTHER INFORMATION: GS linker

<400> SEQUENCE: 38

Gly Gly Gly Ser
1

STABLE FC BINDING PROTEIN, METHOD FOR PRODUCING SAID PROTEIN, AND ANTIBODY ADSORBENT IN WHICH SAID PROTEIN IS USED

REFERENCE TO A SEQUENCE LISTING SUBMITTED VIA EFS-WEB

The instant application contains a Sequence Listing which has been submitted electronically in ASCII format and is hereby incorporated by reference in its entirety. Said ASCII copy, created on Jun. 9, 2022, is named P58843_SL.txt and is 65,978 bytes in size.

FIELD

The present invention relates to an Fc binding protein having an affinity for immunoglobulin. More particularly, a human neonatal Fc receptor (FcRn) having enhanced stability with respect to heat or acid compared to a wild-type, a polynucleotide encoding the receptor, a method for producing a human FcRn utilizing the polynucleotide, and an antibody adsorbent obtained by immobilizing the receptor to an insoluble carrier.

BACKGROUND

An Fc receptor is a group of molecules binding to an Fc region of an immunoglobulin molecule. Individual molecule recognizes a single immunoglobulin isotype by a recognition domain belonging to an immunoglobulin superfamily, or immunoglobulin isotypes of the same group by a recognition domain on the Fc receptor. Accordingly, it is determined which accessory cell is to be recruited in an immune response. The Fc receptor may be further divided into several subtypes including an Fcγ receptor which is a receptor for IgG (immunoglobulin G); an Fcε receptor which binds to an Fc region of IgE; an Fcα receptor which binds to an Fc region of IgA, and the like. Moreover, each receptor is further divided, and as for an Fcγ receptor, the existences of FcγRI, FcγRIIa, FcγRIIb, FcγRIIIa, and FcγRIIIb are reported (NPL 1).

On the other hand, a human neonatal Fc receptor (FcRn) is a major histocompatibility complex (MHC) class I related molecule which is different from the human Fcγ receptor belonging to the immunoglobulin superfamily, and composed of heavy chain (α chain) and a β2 microglobulin (β chain) (NPL 2). The FcRn is involved in a mechanism for recycling IgG and serves to suppress degradation of IgG. In addition, the FcRn binds to the IgG depending on pH, and binds at pH of 6.5 or less (NPL 3).

An amino acid sequence of an α chain (SEQ ID NO: 1) of the human FcRn is disclosed in a public database such as UniProt (Accession number: P55899). In addition, an amino acid sequence of a β chain (SEQ ID NO: 2) is disclosed in UniProt (Accession number: P61769). Further, a structural functional domain of the human FcRn, a signal peptide sequence for penetrating a cellular membrane, and a position of a transmembrane region are similarly disclosed. FIG. 1 illustrates a schematic structural diagram of the α chain of the human FcRn, and FIG. 2 illustrates a schematic structural diagram of the β chain. Note that, an amino acid number in FIG. 1 corresponds to an amino acid number set forth in SEQ ID NO: 1. In other words, in SEQ ID NO: 2, a region form the first methionine (Met) to the 23rd glycine (Gly) is assigned to a signal sequence (S); a region from the 24th alanine (Ala) to the 297th serine (Ser) is assigned to an extracellular region (EC); a region from the 298th valine (Val) to the 321st tryptophan (Trp) is assigned to a transmembrane region (TM); and a region from the 322nd arginine (Arg) to the 365th alanine (Ala) is assigned to an intracellular region (C). In FIG. 2, an amino acid number corresponds to an amino acid number set forth in SEQ ID NO: 2. In other words, in SEQ ID NO: 2, a region from the first methionine (Met) to the 20th alanine (Ala) is assigned to a signal sequence (S); and a region from the 21st isoleucine (Ile) to the 119th methionine (Met) is assigned to a β2 microglobulin (B2M).

CITATION LIST

Non Patent Literature

[NPL1] Takai. T., Jpn. J. Clin. Immunol., 28, 318-326, 2005
[NPL2] N. E. Simister et al., Nature, 337, 184-187, 1989
[NPL3] M. Raghavan et al., Biochemistry, 34, 14649-14657, 1995

SUMMARY

Technical Problem

An object of the present invention is to provide an FcRn having an enhanced stability, particularly to heat or acid, and to provide a method for producing the FcRn.

Solution to Problem

The present inventors have studied intensively to solve the above problem. As a result, the present inventors have identified amino acid residues which involve enhancing the stability in the human FcRn and found that a mutant in which the amino acid residues are substituted with other amino acid(s) has excellent stability with respect to heat or acid. Thus they have attained the present invention.

In other words, the present application encompasses the aspects according to the following <1> to <15>:

<1> An Fc binding protein comprising the amino acid residues from the 24th alanine to the 297th serine in the amino acid sequence set forth in SEQ ID NO: 1 and the amino acid residues from the 21st isoleucine to the 119th methionine of an amino acid sequence set forth in SEQ ID NO: 2, provided that the Fc binding protein includes at least any one of the following mutations (1) to (39) in the amino acid residues:

(1) a mutation in which the 49th valine is substituted with alanine in SEQ ID NO: 1;
(2) a mutation in which the 62nd asparagine is substituted with threonine in SEQ ID NO: 1;
(3) a mutation in which the 71st cysteine is substituted with arginine in SEQ ID NO: 1;
(4) a mutation in which the 78th asparagine is substituted with aspartic acid in SEQ ID NO: 1;
(5) a mutation in which the 79th glutamine is substituted with histidine in SEQ ID NO: 1;
(6) a mutation in which the 80th valine is substituted with aspartic acid in SEQ ID NO: 1;
(7) a mutation in which the 96th lysine is substituted with glutamic acid in SEQ ID NO: 1;
(8) a mutation in which the 103rd lysine is substituted with glutamic acid in SEQ ID NO: 1;
(9) a mutation in which the 125th asparagine is substituted with aspartic acid in SEQ ID NO: 1;

(10) a mutation in which the 127th serine is substituted with proline in SEQ ID NO: 1;
(11) a mutation in which the 151st glycine is substituted with aspartic acid in SEQ ID NO: 1;
(12) a mutation in which the 172nd asparagine is substituted with aspartic acid in SEQ ID NO: 1;
(13) a mutation in which the 173rd lysine is substituted with glutamic acid in SEQ ID NO: 1;
(14) a mutation in which the 180th phenylalanine is substituted with tyrosine in SEQ ID NO: 1;
(15) a mutation in which the 192nd arginine is substituted with leucine in SEQ ID NO: 1;
(16) a mutation in which the 193rd glycine is substituted with aspartic acid in SEQ ID NO: 1;
(17) a mutation in which the 196th asparagine is substituted with aspartic acid in SEQ ID NO: 1;
(18) a mutation in which the 206th arginine is substituted with cysteine in SEQ ID NO: 1;
(19) a mutation in which the 210th arginine is substituted with cysteine in SEQ ID NO: 1;
(20) a mutation in which the 219th leucine is substituted with histidine in SEQ ID NO: 1;
(21) a mutation in which the 220th threonine is substituted with alanine in SEQ ID NO: 1;
(22) a mutation in which the 226th phenylalanine is substituted with serine in SEQ ID NO: 1;
(23) a mutation in which the 232nd glutamine is substituted with leucine in SEQ ID NO: 1;
(24) a mutation in which the 233rd leucine is substituted with proline in SEQ ID NO: 1;
(25) a mutation in which the 255th glycine is substituted with serine in SEQ ID NO: 1;
(26) a mutation in which the 256th serine is substituted with proline in SEQ ID NO: 1;
(27) a mutation in which the 261st serine is substituted with proline in SEQ ID NO: 1;
(28) a mutation in which the 262nd serine is substituted with cysteine in SEQ ID NO: 1;
(29) a mutation in which the 263rd leucine is substituted with proline in SEQ ID NO: 1;
(30) a mutation in which the 266th lysine is substituted with glutamic acid or arginine in SEQ ID NO: 1;
(31) a mutation in which the 267th serine is substituted with proline in SEQ ID NO: 1;
(32) a mutation in which the 273rd tyrosine is substituted with histidine in SEQ ID NO: 1;
(33) a mutation in which the 282nd leucine is substituted with histidine in SEQ ID NO: 1;
(34) a mutation in which the 286th leucine is substituted with histidine in SEQ ID NO: 1;
(35) a mutation in which the 295th lysine is substituted with glutamic acid in SEQ ID NO: 1;
(36) a mutation in which the 32nd arginine is substituted with histidine in SEQ ID NO: 2;
(37) a mutation in which the 42nd phenylalanine is substituted with isoleucine or tyrosine in SEQ ID NO: 2;
(38) a mutation in which the 68th lysine is substituted with glutamic acid in SEQ ID NO: 2;
(39) a mutation in which the 87th tyrosine is substituted with histidine in SEQ ID NO: 2.

<2> The Fc binding protein according to <1>, comprising the amino acid residues consisting of the sequence set forth in SEQ ID NO: 3, provided that the Fc binding protein includes at least any one of the following mutations (1) to (45) in the amino acid residues:
(1) a mutation in which the 152nd valine is substituted with alanine in SEQ ID NO: 3;
(2) a mutation in which the 165th asparagine is substituted with threonine in SEQ ID NO: 3;
(3) a mutation in which the 174th cysteine is substituted with arginine in SEQ ID NO: 3;
(4) a mutation in which the 181st asparagine is substituted with aspartic acid in SEQ ID NO: 3;
(5) a mutation in which the 182nd glutamine is substituted with histidine in SEQ ID NO: 3;
(6) a mutation in which the 183rd valine is substituted with aspartic acid in SEQ ID NO: 3;
(7) a mutation in which the 199th lysine is substituted with glutamic acid in SEQ ID NO: 3;
(8) a mutation in which the 206th lysine is substituted with glutamic acid in SEQ ID NO: 3;
(9) a mutation in which the 228th asparagine is substituted with aspartic acid in SEQ ID NO: 3;
(10) a mutation in which the 230th serine is substituted with proline in SEQ ID NO: 3;
(11) a mutation in which the 254th glycine is substituted with aspartic acid in SEQ ID NO: 3;
(12) a mutation in which the 275th asparagine is substituted with aspartic acid in SEQ ID NO: 3;
(13) a mutation in which the 276th lysine is substituted with glutamic acid in SEQ ID NO: 3;
(14) a mutation in which the 283rd phenylalanine is substituted with tyrosine in SEQ ID NO: 3;
(15) a mutation in which the 295th arginine is substituted with leucine in SEQ ID NO: 3;
(16) a mutation in which the 296th glycine is substituted with aspartic acid in SEQ ID NO: 3;
(17) a mutation in which the 299th asparagine is substituted with aspartic acid in SEQ ID NO: 3;
(18) a mutation in which the 309th arginine is substituted with cysteine in SEQ ID NO: 3;
(19) a mutation in which the 313rd arginine is substituted with cysteine in SEQ ID NO: 3;
(20) a mutation in which the 322nd leucine is substituted with histidine in SEQ ID NO: 3;
(21) a mutation in which the 323rd threonine is substituted with alanine in SEQ ID NO: 3;
(22) a mutation in which the 329th phenylalanine is substituted with serine in SEQ ID NO: 3;
(23) a mutation in which the 335th glutamine is substituted with leucine in SEQ ID NO: 3;
(24) a mutation in which the 336th leucine is substituted with proline in SEQ ID NO: 3;
(25) a mutation in which the 358th glycine is substituted with serine in SEQ ID NO: 3;
(26) a mutation in which the 359th serine is substituted with proline in SEQ ID NO: 3;
(27) a mutation in which the 364th serine is substituted with proline in SEQ ID NO: 3;
(28) a mutation in which the 365th serine is substituted with cysteine in SEQ ID NO: 3;
(29) a mutation in which the 366th leucine is substituted with proline in SEQ ID NO: 3;
(30) a mutation in which the 369th lysine is substituted with glutamic acid or arginine in SEQ ID NO: 3;
(31) a mutation in which the 370th serine is substituted with proline in SEQ ID NO: 3;
(32) a mutation in which the 376th tyrosine is substituted with histidine in SEQ ID NO: 3;
(33) a mutation in which the 385th leucine is substituted with histidine in SEQ ID NO: 3;
(34) a mutation in which the 389th leucine is substituted with histidine in SEQ ID NO: 3;

(35) a mutation in which the 398th lysine is substituted with glutamic acid in SEQ ID NO: 3;
(36) a mutation in which the 14th arginine is substituted with histidine in SEQ ID NO: 3;
(37) a mutation in which the 24th phenylalanine is substituted with isoleucine or tyrosine in SEQ ID NO: 3;
(38) a mutation in which the 50th lysine is substituted with glutamic acid in SEQ ID NO: 3;
(39) a mutation in which the 69th tyrosine is substituted with histidine in SEQ ID NO: 3;
(40) a mutation in which the 107th glycine is substituted with aspartic acid in SEQ ID NO: 3;
(41) a mutation in which the 114th glycine is substituted with aspartic acid in SEQ ID NO: 3;
(42) a mutation in which the 117th glycine is substituted with serine in SEQ ID NO: 3;
(43) a mutation in which the 123rd glycine is substituted with serine or aspartic acid in SEQ ID NO: 3;
(44) a mutation in which the 125th glycine is substituted with aspartic acid in SEQ ID NO: 3;
(45) a mutation in which the 126th serine is substituted with asparagine in SEQ ID NO: 3.

<3> The Fc binding protein according to <2>, includes at least four mutations shown below:
(3) a mutation in which the 174th cysteine is substituted with arginine in SEQ ID NO: 3;
(4) a mutation in which the 181st asparagine is substituted with aspartic acid in SEQ ID NO: 3;
(15) a mutation in which the 295th arginine is substituted with leucine in SEQ ID NO: 3;
(23) a mutation in which the 335th glutamine is substituted with leucine in SEQ ID NO: 3.

<4> The Fc binding protein according to <3> further includes the following mutation:
(11) a mutation in which the 254th glycine is substituted with aspartic acid in SEQ ID NO: 3.

<5> The Fc binding protein according to <4> further includes the following mutation:
(17) a mutation in which the 299th asparagine is substituted with aspartic acid in SEQ ID NO: 3.

<6> The Fc binding protein according to <5> further includes the following mutation:
(35) a mutation in which the 398th lysine is substituted with glutamic acid in SEQ ID NO: 3.

<7> The Fc binding protein according to <6> further includes at least one of the mutations shown below:
(1) a mutation in which the 152nd valine is substituted with alanine in SEQ ID NO: 3;
(12) a mutation in which the 275th asparagine is substituted with aspartic acid in SEQ ID NO: 3;
(19) a mutation in which the 313rd arginine is substituted with cysteine in SEQ ID NO: 3;
(26) a mutation in which the 359th serine is substituted with proline in SEQ ID NO: 3.

<8> The Fc binding protein according to <3>, comprising the amino acid residues consisting of the sequence set forth in any one of SEQ ID Nos: 5 to 7.

<9> A polynucleotide encoding the Fc binding protein according to any one of <1> to <8>.

<10> An expression vector containing the polynucleotide according to <9>.

<11> A transformant obtained by transforming a host with the expression vector according to <10>.

<12> The transformant according to <11>, wherein the host is Escherichia coli.

<13> A method for producing Fc binding protein comprising:
(A) a step of expressing the Fc binding protein by culturing the transformant according to <11> or <12>; and
(B) a step of recovering the expressed Fc binding protein from the culture product.

<14> An adsorbent obtained by immobilizing the Fc binding protein according to any one of <1> to <8> to an insoluble carrier.

<15> A method of separating an antibody, comprising a step of bringing the adsorbent according to <14> into contact with a solution containing the antibody.

The present invention will be hereinafter explained in detail.

The Fc binding protein of the present invention is a protein having a binding property to an Fc region of an antibody, comprising at least the amino acid residues shown in the following (I) and (II), provided that the Fc binding protein includes an amino acid substitution at a specific position in the amino acid residues:
(I) the amino acid residues from the 24th alanine to the 297th serine, which correspond to an extracellular region (EC region in FIG. 1) of a human FcRn α chain consisting of the amino acid sequence set forth in SEQ ID NO: 1;
(II) the amino acid residues from the 21st isoleucine to the 119th methionine, which correspond to a β2 microglobulin region (B2M region in FIG. 2) of a human FcRn β chain consisting of an amino acid sequence set forth in SEQ ID NO: 2.

Accordingly, the Fc binding protein of the present invention may contain all or a part of a signal peptide region (S region in FIG. 1 and FIG. 2) located at the N-terminal side of the extracellular region (EC region in FIG. 1) of the human FcRn α chain or β2 microglobulin region (B2M region in FIG. 2) of the human FcRn β chain, or may contain all or a part of the transmembrane region (TM region in FIG. 1) and the extracellular region (C region in FIG. 1) located at the C-terminal side of the extracellular region (EC region in FIG. 1) of the human FcRn α chain.

In this specification, the Fc binding protein comprising at least the amino acid residues shown in the above-described (I) and the above-described (II) may be acceptable so long as it comprises at least the amino acid sequence shown in the above-described (I) and the amino acid sequence shown in the above-described (II) in the amino acid sequence of the protein, and may be an aspect in which the amino acid residues shown in the above-described (I) are directly linked to the amino acid residues shown in the above-described (II) or an aspect in which the amino acid residues shown in the above-described (I) are linked to the amino acid residues shown in the above-described (II) via a known linker such as a GS linker (a linker composed of a repetitive sequence of GGGS (SEQ ID NO.:38)).

In the present specification, a "wild-type FcRn" includes not only a naturally occurring FcRn but also an FcRn which comprises at least the amino acid residues shown in the above-described (I) and the above-described (II) and has no mutation (substitution, deletion, insertion, or addition of an amino acid) in the amino acid residues shown in the above-described (I) and the above-described (II). Specifically, examples include FcRn comprising the amino acid sequence (e.g., SEQ ID NO: 3) in which the amino acid residues shown in the above-described (I) and the above-described (II) are linked via a linker sequence, and the like.

A preferred aspect of the Fc binding protein comprising at least the amino acid residues shown in the above-described (I) and the above-described (II) includes an Fc binding protein comprising the amino acid residues consisting of the sequence set forth in SEQ ID NO: 3. In SEQ ID NO: 3, a region from the 3rd isoleucine to the 101th methionine corresponds to the β2 microglobulin region (a region from the 21st isoleucine to the 119th methionine in SEQ ID NO: 2) of the human FcRn β chain, a region from the 102nd glycine to the 126th serine corresponds to the GS linker, a region from the 127th alanine to the 400th serine corresponds to the extracellular region (a region from the 24th alanine to the 297th serine in SEQ ID NO: 1) of the human FcRn α chain.

An amino acid substitution at the above-described specific position, specifically when the Fc binding protein comprising at least the amino acid residues shown in the above-described (I) and the above-described (II) is an Fc binding protein consisting of the sequence set forth in SEQ ID NO: 3, is at least any one of the following substitutions: Arg14His (this expression indicates that the 14th arginine is substituted with histidine in SEQ ID NO: 3, the same applies hereafter), Phe24Ile, Phe24Tyr, Lys50Glu, Tyr69His, Gly107Asp, Gly114Asp, Gly117Ser, Gly123Ser, Gly123Asp, Gly125Asp, Ser126Asn, Val152Ala, Asn165Thr, Cys174Arg, Asn181Asp, Gln182His, Val183Asp, Lys199Glu, Lys206Glu, Asn228Asp, Ser230Pro, Gly254Asp, Asn275Asp, Lys276Glu, Phe283Tyr, Arg295Leu, Gly296Asp, Asn299Asp, Arg309Cys, Arg313Cys, Leu322His, Thr323Ala, Phe329Ser, Gln335Leu, Leu336Pro, Gly358Ser, Ser359Pro, Ser364Pro, Ser365Cys, Leu366Pro, Lys369Glu, Lys369Arg, Ser370Pro, Tyr376His, Leu385His, Leu389His, and Lys398Glu. Note that the amino acid residue positions of the above-described amino acid substitutions in SEQ ID 1 and 2 are shown in Table 1.

TABLE 1

| Amino Acid Substitution | Position of Amino Acid Residues | | |
|---|---|---|---|
| | SEQ ID NO: 1 | SEQ ID NO: 2 | SEQ ID NO: 3 |
| (1) Val152Ala | 49 | — | 152 |
| (2) Asn165Thr | 62 | — | 165 |
| (3) Cys174Arg | 71 | — | 174 |
| (4) Asn181Asp | 78 | — | 181 |
| (5) Gln182His | 79 | — | 182 |
| (6) Val183Asp | 80 | — | 183 |
| (7) Lys199Glu | 96 | — | 199 |
| (8) Lys206Glu | 103 | — | 206 |
| (9) Asn228Asp | 125 | — | 228 |
| (10) Ser230Pro | 127 | — | 230 |
| (11) Gly254Asp | 151 | — | 254 |
| (12) Asn275Asp | 172 | — | 275 |
| (13) Lys276Glu | 173 | — | 276 |
| (14) Phe283Tyr | 180 | — | 283 |
| (15) Arg295Leu | 192 | — | 295 |
| (16) Gly296Asp | 193 | — | 296 |
| (17) Asn299Asp | 196 | — | 299 |
| (18) Arg309Cys | 206 | — | 309 |
| (19) Arg313Cys | 210 | — | 313 |
| (20) Leu322His | 219 | — | 322 |
| (21) Thr323Ala | 220 | — | 323 |
| (22) Phe329Ser | 226 | — | 329 |
| (23) Gln335Leu | 232 | — | 335 |
| (24) Leu336Pro | 233 | — | 336 |
| (25) Gly358Ser | 255 | — | 358 |
| (26) Ser359Pro | 256 | — | 359 |
| (27) Ser364Pro | 261 | — | 364 |
| (28) Ser365Cys | 262 | — | 365 |
| (29) Leu366Pro | 263 | — | 366 |
| (30) Lys369Glu, Lys369Arg | 266 | — | 369 |
| (31) Ser370Pro | 267 | — | 370 |
| (32) Tyr376His | 273 | — | 376 |

TABLE 1-continued

| Amino Acid Substitution | Position of Amino Acid Residues | | |
|---|---|---|---|
| | SEQ ID NO: 1 | SEQ ID NO: 2 | SEQ ID NO: 3 |
| (33) Leu385His | 282 | — | 385 |
| (34) Leu389His | 286 | — | 389 |
| (35) Lys398Glu | 295 | — | 398 |
| (36) Arg14His | — | 32 | 14 |
| (37) Phe24Ile, Phe24Tyr | — | 42 | 24 |
| (38) Lys50Glu | — | 68 | 50 |
| (39) Tyr69His | — | 87 | 69 |
| (40) Gly107Asp | — | — | 107 |
| (41) Gly114Asp | — | — | 114 |
| (42) Gly117Ser | — | — | 117 |
| (43) Gly123Ser, Gly123Asp | — | — | 123 |
| (44) Gly125Asp | — | — | 125 |
| (45) Ser126Asn | — | — | 126 |

When the Fc binding protein of the present invention is produced by an amino acid substitution, the amino acid residues at the position other than the above-described specific position may be substituted with the amino acid other than those described above so long as it has an antibody avidity. Examples include a conservative substitution generated between amino acids in which both or either of physical property and/or chemical property of the both amino acids are similar to each other. It is known to those skilled in the art that, in the conservative substitution, a function of the protein is maintained generally, not limited to the Fc binding protein, between the one without the substitution generated and the other with the substitution generated. Examples of the conservative substitution includes a substitution generated between glycine and alanine, aspartic acid and glutamic acid, serine and proline, or glutamic acid and alanine (Structure and Function of Protein, MEDICAL SCIENCES INTERNATIONAL, LTD., 9, 2005).

In the Fc binding protein of the present invention, the number of the amino acid is not particularly limited. Examples include the Fc binding proteins shown in the following (a) to (c). These Fc binding proteins are preferred in that the stability with respect to heat or acid is enhanced.

(a) An Fc binding protein which comprises the amino acid residues consisting of the sequence set forth in SEQ ID NO: 3, provided that the Fc binding protein includes substitutions of Cys174Arg, Asn181Asp, Arg295Leu, and Gln335Leu in the amino acid residues (an Fc binding protein comprising the amino acid residues consisting of the sequence set forth in SEQ ID NO: 5).

(b) An Fc binding protein which comprises the amino acid residues consisting of the sequence set forth in SEQ ID NO: 3, provided that the Fc binding protein includes substitutions of Cys174Arg, Asn181Asp, Gly254Asp, Arg295Leu, Asn299Asp, Gln335Leu, and Lys398Glu in the amino acid residues (an Fc binding protein comprising the amino acid residues consisting of the sequence set forth in SEQ ID NO: 6).

(c) An Fc binding protein which comprises the amino acid residues consisting of the sequence set forth in SEQ ID NO: 3, provided that the Fc binding protein includes substitutions of Val152Ala, Cys174Arg, Asn181Asp, Gly254Asp, Arg295Leu, Asn299Asp, Gln335Leu, and Lys398Glu in the amino acid residues (an Fc binding protein comprising the amino acid residues consisting of the sequence set forth in SEQ ID NO: 7).

The Fc binding protein of the present invention may be further added with an oligopeptide which is useful in being separated from a solution in the presence of foreign substances at its N-terminal side or C-terminal side. Examples of the oligopeptide include polyhistidine, polylysine, polyarginine, polyglutamic acid, polyaspartic acid and the like. Further, a cysteine-containing oligopeptide which is useful in immobilizing the Fc binding protein of the present invention to a solid phase such as a support for chromatography may be added at the N-terminal side or C-terminal side of the Fc binding protein of the present invention. The length of the oligopeptide to be added at the N-terminal side or C-terminal side of Fc binding protein is not particularly limited so long as it does not impair the IgG binding property or stability of the Fc binding protein of the present invention. The number of peptides constituting the oligopeptide may be, for example, 2 or more, preferably 4 or more, and more preferably 6 or more. Further, it may be 20 or less, preferably 15 or less, and more preferably 10 or less. When the oligopeptide is added to the Fc binding protein of the present invention, it may be added at the N-terminal side or C-terminal side of the Fc binding protein in a genetic engineering fashion using a method well known to those skilled in the art after a polynucleotide encoding the oligopeptide is produced. Alternatively, the oligopeptide which is chemically synthesized may be chemically bonded and added at the N-terminal side or C-terminal side of the Fc binding protein of the present invention. Further, at the N-terminal side of the Fc binding protein of the present invention, the signal peptide may be added to promote efficient expression in the host. Examples of the signal peptide when the host is *E. coli* may include signal peptides such as PelB, DsbA, MalE (a region from the first to the 26th of the amino acid sequence set forth in UniProt No. P0AEX9), TorT, which make a periplasm secrete a protein (Japanese Unexamined Patent Publication (Kokai) No. 2011-097898).

Examples of a method for producing the polynucleotide of the present invention include:
(i) a method which includes converting an amino acid sequence of the Fc binding protein of the present invention to a nucleotide sequence to artificially synthesize a polynucleotide containing the nucleotide sequence; and
(ii) a method which includes directly, artificially preparing a polynucleotide containing a whole or partial sequence of the Fc binding protein or preparing it, for example, from cDNA of the Fc binding protein using a DNA amplification method such as a PCR method and linking the prepared polynucleotide by an appropriate method. In the method (i), when the amino acid sequence is converted into the nucleotide sequence, it is preferred to convert considering the codon usage in the host to be transformed. As an example, when the host is *E. coli* (*Escherichia coli*), since AGA/AGG/CGG/CGA for arginine (Arg), ATA for isoleucine (Ile), CTA for leucine (Leu), GGA for glycine (Gly), and CCC for proline (Pro) are less frequently used (so-called rare codons), conversion may be performed avoiding these codons. The codon usage may also be analyzed utilizing a public database (e.g., Codon Usage Database available at the website of Kazusa DNA Research Institute). In the polynucleotide of the present invention, an α chain and a β chain may be individually expressed, or the α chain and the β chain may be linked via a linker. Examples of the latter include a polynucleotide consisting of the sequence set forth in SEQ ID NO: 4 which is a polynucleotide encoding a protein consisting of the sequence set forth in SEQ ID NO: 3 which is an Fc binding protein containing the α chain of the human FcRn and the τ3 chain linked via a GS linker.

When a mutation is introduced into the polynucleotide of the present invention, an error-prone PCR method may be used. The reaction conditions in the error-prone PCR method are not particularly limited so long as a desired mutation can be introduced into the polynucleotide encoding the Fc binding protein. For example, the concentrations of 4 types of deoxynucleotides (dATP/dTTP/dCTP/dGTP) which are substrates are made heterogeneous, and $MnCl_2$ is added to the PCR reaction solution at a concentration from 0.01 to 10 mM (preferably from 0.1 to 1 mM) to perform PCR, thereby introducing a mutation into the polynucleotide. Further, examples of a method of introducing a mutation other than the error-prone PCR method include a method in which the polynucleotide containing a whole or partial sequence of the Fc binding protein is contacted and reacted with an agent as a mutagen or irradiated with UV light to introduce a mutation into the polynucleotide for production. In the method, as the agent used as the mutagen, a mutagenic agent which is ordinarily used by those skilled in the art such as hydroxylamine, N-methyl-N'-nitro-N-nitrosoguanidine, nitrous acid, sulfurous acid, hydrazine may be used.

The host to express the Fc binding protein of the present invention is not particularly limited. Examples include, for example, animal cells (CHO cell, HEK cell, Hela cell, COS cell, etc.), yeast (*Saccharomyces cerevisiae, Pichia pastoris, Hansenula polymorpha, Schizosaccharomyces japonicus, Schizosaccharomyces octosporus, Schizosaccharomyces pombe*, etc.), insect cells (Sf9, Sf21, etc.), *E. coli* (JM109 strain, BL21 (DE3) strain, W3110 strain, etc.), and *Bacillus subtilis*. It is preferable to use animal cells or *E. coli* as the host in terms of productivity, and more preferable to use *E. coli* as the host.

When the polynucleotide of the present invention is used to transform the host, the polynucleotide of the present invention per se may be used, but an expression vector (e.g., a bacteriophage, cosmid, plasmid or the like which are usually used for transformation of a prokaryotic cell or an eukaryotic cell) into which the polynucleotide of the present invention are inserted at an appropriate position is more preferably used. The expression vector is not particularly limited so long as it can stably exist and replicate in the host to be transformed. When *E. coli* is used as the host, a pET plasmid vector, a pUC plasmid vector, a pTrc plasmid vector, a pCDF plasmid vector, and a pBBR plasmid vector may be mentioned. The appropriate position means a position which does not destroy a replication function of the expression vector, a desired antibiotic marker, a region involved in transmissibility. When the polynucleotide of the present invention is inserted into the expression vector, it is preferably inserted while linked to a functional polynucleotide such as a promoter needed for the expression. Examples of the promoter when the host is *E. coli* include a trp promoter, a tac promoter, a trc promoter, a lac promoter, a T7 promoter, a recA promoter, and a lpp promoter, and further include a λPL promoter and a λPR promoter of a λ phage; and examples when the host is an animal cell include a SV40 promoter, a CMV promoter, and a CAG promoter.

In order to transform the host using an expression vector (hereinafter referred to as the expression vector of the present invention) into which the polynucleotide of the present invention produced by the method is inserted, a method those skilled in the art ordinary used may be used. For example, when microorganism belonging to the *Escherichia* (*E. coli* JM109 strain, *E. coli* BL21 (DE3) strain, *E. coli* W3110 strain, etc.) is selected as the host, transformation may be performed, for example, using a method described in the known reference (e.g., Molecular Cloning, Cold Spring Harbor Laboratory, 256, 1992). When the host is an animal cell, electroporation or lipofection may be used. A transformant obtained by transformation using the above-described method may be screened by an appropriate method to obtain a transformant (hereinafter referred to as a transformant of the present invention) which can express the Fc binding protein of the present invention.

In order to prepare the expression vector of the present invention from the transformant of the present invention, the expression vector of the present invention may be extracted and prepared from the transformant of the present invention by a method suitable for the host which has been used for the transformation. For example, when the host of the transformant of the present invention is $E.$ $coli$, it may be prepared from the culture product obtained by culturing the transformant using an alkali extraction method or a commercially available extraction kit such as QIAprep Spin Miniprep kit (manufactured by Qiagen N. V.) or the like.

The Fc binding protein of the present invention may be produced by culturing the transformant of the present invention, and recovering the Fc binding protein of the present invention from the culture product. In this specification, the culture product includes the cell of the cultured transformant of the present invention itself, as well as a culture medium used for culture. The transformant used in the method for producing protein of the present invention may be cultured in a culture medium suitable for culturing the host of interest. When the host is $E.$ $coli$, examples of a preferred medium include a LB (Luria-Bertani) medium supplemented with nutrient source. In order to selectively proliferate the transformant of the present invention based on the presence or absence of the introduced expression vector of the present invention, it is preferred to culture with an agent corresponding to the drug resistant gene contained in the vector added to the medium. For example, when the vector contains a kanamycin resistant gene, kanamycin may be added to the medium. Moreover, in addition to a source of carbon, nitrogen and inorganic salt but a suitable nutrient source may be added to the medium, and optionally one or more reducing agents selected from the group consisting of glutathione, cysteine, cystamine, thioglycolate and dithiothreitol may be included. Furthermore, a reagent may be added such as glycine which may promote a secretion of protein from the transformant to a culture solution. Specifically, when the host is $E.$ $coli$, it is preferred to add glycine in an amount of 2% (w/v) or less relative to the medium. The culture temperature when the host is $E.$ $coli$ is generally 10° C. to 40° C., preferably 20° C. to 37° C., and more preferably around 25° C., but may be selected depending on the characteristic of the protein to be expressed. The pH of the medium when the host is $E.$ $coli$ is pH 6.8 to pH 7.4, preferably around pH 7.0. Further, when an inducible promoter is contained in the vector of the present invention, it is preferred to perform induction under the conditions so as to enable favorable expression of the Fc binding protein of the present invention. Examples of an inducer may include IPTG (isopropyl-β-D-thiogalactopyranoside). When the host is $E.$ $coli$, turbidity (absorbance at 600 nm) of the culture solution is measured, and when the turbidity reaches about 0.5 to 1.0, an appropriate amount of IPTG is added and culture is continued to induce expression of the Fc binding protein. The concentration of the added IPTG may be suitably selected from the range of 0.005 to 1.0 mM, but preferably from the range of 0.01 to 0.5 mM. Various conditions for induction of IPTG may be those well known in the art.

In order to recover the Fc binding protein of the present invention from the culture product obtained by culturing the transformant of the present invention, the Fc binding protein of the present invention may be recovered by separating/purifying it from the culture product using the method suitable for the expressed form of the Fc binding protein of the present invention in the transformant of the present invention. For example, when expressed into a culture supernatant, bacterial cells are separated by centrifugal procedure, and the Fc binding protein of the present invention may be purified from the resulting culture supernatant. Further, when expressed in a cell (including periplasm), bacterial cells are collected by centrifugal procedure, then the bacterial cells are disrupted by, for example adding an enzymatic treatment agent or a surfactant or using an ultrasonic wave or a french press, the Fc binding protein of the present invention may be extracted and then purified. For purification of the Fc binding protein of the present invention, a method known in the art may be used. Examples include separation/purification using liquid chromatography. Examples of the liquid chromatography include ion exchange chromatography, hydrophobic interaction chromatography, gel filtration chromatography, affinity chromatography and the like. The Fc binding protein of the present invention may be prepared with high purity by performing a purification operation using such chromatography in combination.

In order to measure an avidity of the resulting Fc binding protein of the present invention to the IgG, for example, an avidity to the IgG may be measured by using the Enzyme-Linked ImmunoSorbent Assay (hereinafter referred to as ELISA) method or a surface plasmon resonance method. As IgG used for measurement of the avidity, a human IgG is preferred, and a human IgG1 and a human IgG3 are particularly preferred.

The adsorbent of the present invention can be produced by immobilizing the Fc binding protein of the present invention to the insoluble carrier. The insoluble carrier is not particularly limited, and examples include a carrier produced from polycarbohydrate such as agarose, alginate (alginic acid salt), carrageenan, chitin, cellulose, dextrin, dextran, starch; a carrier produced form synthetic polymer such as polyvinyl alcohol, polymethacrate, poly(2-hydroxyethylmethacrylate), polyurethane; and a carrier produced from ceramics such as silica. Among them, a carrier produced from polycarbohydrate and a synthetic high molecule are preferred as insoluble carriers. Examples of the preferred carrier include a polymethacrylate gel with a hydroxyl group introduced therein such as Toyopearl (manufactured by Tosoh Corporation), an agarose gel such as Sepharose (manufactured by GE Healthcare), and a cellulose gel such as Cellfine (manufactured by JNC). The shape of the insoluble carrier is not particularly limited, and may be any of particular, non-particular, porous, or non-porous.

In order to immobilize the Fc binding protein to the insoluble carrier, an active group such as a N-Hydroxysuccinimide (NHS) activated ester group, an epoxy group, a carboxyl group, a maleimide group, a haloacetyl group, a tresyl group, a formyl group, or haloacetamide is imparted to the insoluble carrier, and the human Fc binding protein may be covalently bonded and thus immobilized to the insoluble carrier via the active group. As the active group-imparted carrier, a commercially available carrier may be used as it is. Alternatively, an active group may be introduced into the surface of the carrier under an appropriate reaction condition to prepare the active group imparted carrier. Examples of the commercially available active group-imparted carrier include TOYOPEARL AF-Epoxy-650M, TOYOPEARL AF-Tresyl-650M (all of which are manufactured by Tosoh Corporation), HiTrap NHS-activated HP Columns, NHS-activated Sepharose 4 Fast Flow, Epoxy-activated Sepharose 6B (all of which are manufactured by GE Healthcare), SulfoLink Coupling Resin (manufactured by ThermoFisher Scientific).

On the other hand, examples of a method of introducing an active group into the surface of the carrier may include a method in which one of the two or more active moieties possessed by a compound is reacted with a hydroxyl group, an epoxy group, a carboxyl group, an amino group or the like present on the surface of the carrier. Among the exemplary compounds, a compound which introduces an epoxy group into a hydroxyl group or an amino group of the surface of the carrier is exemplified by epichlorohydrin, ethanediol diglycidyl ether, butanediol diglycidyl ether, and hexanediol diglycidyl ether. Examples of a compound which introduces a carboxyl group into the surface of the carrier after the epoxy group is introduced into the surface of the carrier by the compound may include 2-mercaptoacetic acid, 3-mercaptopropionic acid, 4-mercaptobutyric acid, 6-mercaptobutyric acid, glycine, 3-aminopropionic acid, 4-aminobutyric acid, and 6-aminohexanoic acid.

Examples of a compound which introduces a maleimide group into a hydroxyl group, an epoxy group, a carboxyl group, or an amino group present on the surface of the carrier include N-(ε-maleimidocaproic acid)hydrazide, N-(ε-maleimidopropionic acid)hydrazide, 4-(4-N-maleimidophenyl)acetic acid hydrazide, 2-aminomaleimide, 3-aminomaleimide, 4-aminomaleimide, 6-aminomaleimide, 1-(4-aminophenyl)maleimide, 1-(3-aminophenyl)maleimide, 4 (maleimido)phenylisocyanate, 2-maleimidoacetic acid, 3-maleimidopropionic acid, 4-maleimidobutyric acid, 6-maleimidohexanoic acid, (N-[α-maleimidoacetoxy])succinimide ester, (m-maleimidobenzoyl) N-hydroxysuccinimide ester, (succinimidyl-4-[maleimidomethyl])cyclohexan-1-carbonyl-[6-aminohexanoic acid], (succinimidyl-4-[maleimidomethyl])cyclohexan-1-carboxylic acid, (p-maleimidobenzoyl) N-hydroxysuccinimide ester, and (m-maleimidobenzoyl) N-hydroxysuccinimide ester.

Examples of a compound which introduces a haloacetyl group into a hydroxyl group or an amino group present on the surface of the carrier include chloroacetic acid, bromoacetic acid, iodoacetic acid, chloroacetic acid chloride, bromoacetic acid chloride, bromoacetic acid bromide, chloroacetic acid anhydride, bromoacetic acid anhydride, iodoacetic acid anhydride, 2-(iodoacetamide)acetic acid-N-hydroxysuccinimide ester, 3-(bromoacetamide)propionic acid-N-hydroxysuccinimide ester, 4-(iodoacetyl)aminobenzoic acid-N-hydroxysuccinimide ester. In addition, a method in which a hydroxyl group or an amino group present on the surface of the carrier is reacted with ω-alkenylalkaneglycidyl ether, and then ω-alkenyl moiety is halogenated with a halogenating agent for activation may be mentioned. Examples of the ω-alkenylalkane glycidyl ether include allylglycidyl ether, 3-butenylglycidyl ether, and 4-pentenylglycidyl ether; and examples of a halogenating agent include N-chlorosuccinimide, N-bromosuccinimide, and N-iodosuccinimide.

Other examples of a method of introducing an active group into the surface of the carrier include a method of introducing an activating group into a carboxyl group present on the surface of the carrier using a condensing agent and an additive. Examples of the condensing agent may include 1-ethyl-3-(3-dimethylaminopropyl)carbodiimide (EDC), and dicyclohexylcarbodiamide, carbonyl diimidazole. Examples of the additive include N-hydroxysuccinic acid imide (NHS), 4-nitrophenol, and 1-hydroxybenztriazole.

Examples of a buffer used to immobilize the Fc binding protein of the present invention to the insoluble carrier include an acetate buffer, a phosphate buffer, a MES (2-Morpholinoethanesulfonic acid) buffer, a HEPES (4-(2-hydroxyethyl)-1-piperazineethanesulfonic acid) buffer, a Tris buffer, and a borate buffer. The reaction temperature for immobilization is appropriately set from the temperature range of 5° C. to 50° C. considering the reactivity of the active group and the stability of the Fc binding protein of the present invention, and is preferably in the range from 10° C. to 35° C.

In order to separate an antibody using the adsorbent of the present invention which is obtained by immobilizing the Fc binding protein of the present invention to the insoluble carrier, for example, a buffer containing an antibody is added to a column filled with the adsorbent of the present invention using a liquid supplying device such as a pump to bring the buffer into contact with the adsorbent of the present invention. Thereby, the antibody is specifically adsorbed to the adsorbent of the present invention, and then an appropriate eluate is added to the column to elute the antibody. It is preferred to equilibrate the column using an appropriate buffer before a buffer containing an antibody is added to the column since the antibody with higher purity can be separated. Examples of a buffer include a buffer containing an inorganic salt as an ingredient such as a phosphoric acid buffer. The pH of the buffer is pH 3 to 10, preferably pH 4 to 8, and more preferably pH 5 to 6. In order to elute the antibody adsorbed to the adsorbent of the present invention, it is sufficient to weaken the interaction between the antibody and a ligand (the Fc binding protein of the present invention), specifically, by the change in pH by a buffer, a counter-peptide, the change in the temperature, and the change in the salt concentration, for example. Specific examples of the eluate to elute the antibody adsorbed to the adsorbent of the present invention include a buffer more acidic than the solution used to adsorb the antibody to the adsorbent of the present invention, and a buffer having pH around neutral. Examples of the type of the buffer include those having a buffering capacity on the acidic side, such as a citrate buffer, a glycine-HCl buffer, and an acetate buffer; and those having a buffering capacity at the pH near neutral such as a phosphoric acid buffer, a HEPSE buffer, and a Tris-HCl buffer. The pH of the buffer may be set so as not to impair the function of the antibody, and is preferably pH 2.5 to 6.0, more preferably pH 3.0 to 5.0, and still more preferably pH 3.3 to 4.0, or for the pH near neutral, preferably pH 6.0 to 10.0, more preferably pH 7.0 to 9.0, and still more preferably pH 7.5 to 8.5.

In separating the antibody from the solution containing the antibody using the adsorbent of the present invention, the elution position (elution fraction) of the antibody varies depending on the difference in the structure of the amino acid sequence contained in the antibody, for example. Therefore, when the antibody is separated using the adsorbent of the present invention, the difference in structure of the antibody can be discriminated. The discriminable structure is not particularly limited, and as an example, it can also be utilized for separation according to the difference in structure when the antibody is expressed using as a host a cell derived from an animal such as a CHO cell; or yeast such as *Pichia* yeast or *Saccharomyces* yeast.

It is previously described that the difference of the structure of the antibody can be discriminated using the adsorbent of the present invention. However, even when the Fc receptor other than the FcRn (FcγRI, FcγRIIa, FcγRIIb, FcγRIIIa, FcγRIIIb) is used as the Fc binding protein used for the adsorbent, the difference in the structure can also be similarly discriminated. The FcRn contributes a mechanism for recycling an antibody in blood, plays a role in suppressing the degradation of the antibody, and has a high affinity for an antibody which is resistant to degradate in blood, that is, an antibody which can remain effective in blood for a long period of time. Accordingly, a method of separating an antibody using the FcRn as the Fc receptor is suitable for analysis, fractionation, and separation of the antibody which can remain effective for a long period of time.

Advantageous Effects of Invention

The Fc binding protein of the present invention is a protein in which the amino acid residues at the specific position in the extracellular region of the human FcRn α chain and/or the β2 microglobulin region of the human FcRn β chain is substituted with other amino acid residues. The Fc binding protein of the present invention has an enhanced stability with respect to heat and acid compared to the wild-type human FcRn. When the separation of the antibody is performed using the Fc binding protein as an affinity ligand, the Fc binding protein is exposed to an acidic eluate for adsorption/desorption of the target antibody and for washing/regeneration of the column. Therefore, enhancement of the stability with respect to acid can ensure stable separation for a long period of time. In addition, when the Fc binding protein is industrially produced, a production method in which an expression vector which contains a base sequence encoding the Fc binding protein is transformed into *E. coli* is efficient, but it is desirable to suppress inactivation and denaturation of the Fc binding protein, considering the stability of the Fc binding protein during the culture and extraction/purification using the production method. Accordingly, since the heat resistance is enhanced, the Fc binding protein of the present invention can be applied to the production method using *E. coli*. Therefore, the Fc binding protein of the present invention is useful as a ligand for an adsorbent to separate immunoglobulin.

EXAMPLES

Figure 1:
FIG. 1 is a schematic structural diagram of an α-chain of a human FcRn. Numeral in the FIG. indicates the amino acid sequence number set forth in SEQ ID NO: 1. In the figure, S indicates a signal sequence, EC indicates an extracellular region, TM indicated a transmembrane region, and C indicates an intracellular region.
Figure 2:
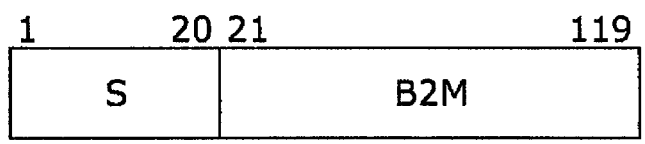
FIG. 2 is a schematic structural diagram of a β-chain of the human FcRn. Numeral in the figure indicates the amino acid sequence number set forth in SEQ ID NO: 2. In the figure, S indicates a signal sequence and B2M indicates a β2 microglobulin.

Hereinafter, Examples will be provided to explain the present invention in more detail, but the present invention is not limited to the Examples.

Example 1 Preparation of a Human FcRn Expression Vector (*E. coli*-Type Codon)

(1) A codon was transformed from a human-type into an *E. coli*-type using a DNAworks method (Nucleic Acids Res., 30, e43, 2002) based on the amino acid sequence from the 24th alanine to the 297th serine of the amino acid sequence of the α-chain of the human FcRn set forth in SEQ ID NO: 1, and the amino acid sequence from the 21st isoleucine to the 119th methionine of the amino acid sequence of the β-chain of the human FcRn composed of the amino acid sequence set forth in SEQ ID NO: 2, and a nucleotide sequence which encodes a GS linker was inserted between the transformed nucleotide sequences to design the nucleotide sequence set forth in SEQ ID NO: 4.

(2) A polynucleotide composed of a sequence in which a NcoI recognition sequence (CCATGG) was added to the 5'-terminal side and a HindIII recognition sequence (AAGCTT) was added to the 3'-terminal side of the designed nucleotide sequence (SEQ ID NO: 4) was artificially synthesized.

(3) After the polynucleotide synthesized in (2) was digested with restriction enzymes NcoI and HindIII, the resultant was ligated to an expression vector pETMalE (Japanese Unexamined Patent Publication (Kokai) No. 2011-206046) which had been previously digested with the restriction enzyme NcoI and HindIII, and *E. coli* BL21 (DE3) strain was transformed using the resulting ligation product.

(4) After the resulting transformant was cultured in a LB medium containing 50 μg/mL of kanamycin, a QIAprep Spin Miniprep kit (manufactured by Qiagen N. V.) was used to extract the expression vector pET-eFcRn of a human FcRn which is a wild-type Fc binding protein.

(5) Of the expression vector pET-eFcRn prepared in (4), a cycle sequence reaction of a polynucleotide encoding the FcRn and a surrounding region thereof are performed using a Big Dye Terminator Cycle Sequencing FS read Reaction kit (manufactured by ThermoFisher Scientific) based on α chain terminator method, and the nucleotide sequence was analyzed using a full-automatic DNA sequencer ABI Prism 3700 DNA analyzer (manufactured by ThermoFisher Scientific). In the analysis, an oligonucleotide set forth in SEQ ID NO: 8 (5'-TAATACGACTCACTATAGGG-3') or SEQ ID NO: 9 (5'-TATGCTAGTTATTGCTCAG-3') was used as a primer for sequencing.

The amino acid sequence of the polypeptide expressed with an expression vector pET-eFcRn is shown in SEQ ID NO: 10 and the sequence of the polynucleotide encoding the polypeptide is shown in SEQ ID NO: 11, respectively. In SEQ ID NO: 10, a region from the first methionine (Met) to the 26th alanine (Ala) is a MalE signal peptide, a region from the 27th lysine (Lys) to the 33rd glycine (Gly) is a linker sequence, a region from the 34th isoleucine (Ile) to the 132nd methionine (Met) is a β2 microglobulin region of the human FcRn β chain (a region from the 21st to the 119th in SEQ ID NO: 2), a region from the 133rd glycine (Gly) to the 157th serine (Ser) is a GS linker sequence, a region from the 158th alanine (Ala) to the 431st serine (Ser) is an extracellular region of the human FcRn α chain (a region from the 24th to the 297th in SEQ ID NO: 1), and a region from the 432nd to the 437th histidine (His) is a tag sequence.

Example 2 Measurement of Antibody Binding Activity of Human FcRn (1) The *E. coli* BL21 (DE3) strain transformed with the expression vector pET-eFcRn, obtained in Example 1 was inoculated in 4 mL of 2YT liquid medium (peptone, 16 g/L; yeast extract, 10 g/L; sodium chloride, 5 g/L) containing 50 μg/mL of kanamycin, and subsequently a shaking culture was performed aerobically at 37° C. overnight to perform the pre-culture.

(2) The pre-cultured solution (1) (150 μL) was inoculated in 15 mL of 2YT liquid medium to which 50 μg/mL of kanamycin had been added, and a shaking culture was performed aerobically at 37° C.

(3) One hundred and fifty minutes after the beginning of the culture, IPTG was added to the concentration of 0 mM/0.1 mM, and a shaking culture was performed at 20° C. for 4 hours.

(4) After the culture was completed, the bacterial cells were harvested by centrifugation, and a protein extract in a soluble fraction was prepared using an ultrasonic generator (manufactured by TOMY SEIKO CO., LTD.).

(5) The antibody avidity of the human FcRn contained in the protein extract prepared in (4) was measured using the ELISA method shown below.

(5-1) A gamma globulin preparation (manufactured by The Chemo-Sero-Therapeutic Research Institute) which is a human antibody was immobilized to wells of a 96-well microplate at 10 μg/well (at 4° C. for 18 hours). After completion of the immobilization, blocking was performed using a phosphate buffer (pH 6.0) containing 2% (w/v) of SKIM MILK (manufactured by Becton, Dickinson and Company) and 150 mM sodium chloride.

(5-2) After washing with a washing buffer (a phosphate buffer (pH 6.0) containing 150 mM sodium chloride), the solution containing the human FcRn prepared in (4) was reacted with an immobilized gamma globulin (at 30° C. for 1 hour).

(5-3) After completion of the reaction, Anti-6His antibody (manufactured by Bethyl Laboratories, Inc.) which had been washed with the washing buffer and diluted with a blocking solution to 100 ng/mL was added at 100 μL/well.

(5-4) After reacted at 30° C. for 1 hour and washed with the washing buffer, TMB Peroxidase Substrate (manufactured by Kirkegaard and Perry Laboratories, Inc.) was added at 50 μL/well. The coloring was stopped by adding 1M phosphoric acid at 50 μL/well, and the absorbance at 450 nm was measured with a microplate reader (manufactured by Tecan Trading AG).

Figure 3:
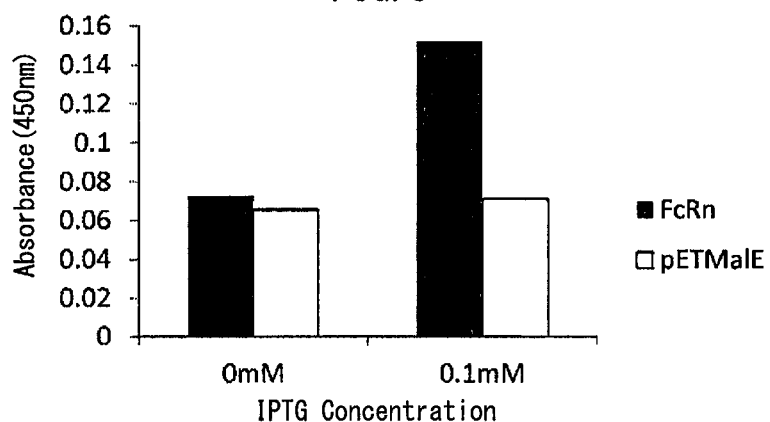
FIG. 3 is a diagram illustrating a binding property of the human FcRn to the human IgG expressed with a transformant obtained in Example 1.

A diagram summarizing the relation of the absorbance (450 nm) corresponding to an antibody avidity when a solution containing the human FcRn prepared in (4) was added is shown as FIG. 3. In FIG. 3, pETMalE is the one obtained by similarly culturing and extracting a plasmid without an FcRn gene inserted therein (a negative control). Since the absorbance is increased when the FcRn is inserted compared to the case where the FcRn gene is not inserted, it is recognized that the human FcRn is expressed in an active state.

Example 3 Introduction of Mutation into Fc Binding Protein and Preparation of Library A mutation was randomly introduced by an error-prone PCR into a polynucleotide encoding the Fc binding protein of the Fc binding protein expression vector pET-eFcRn prepared in Example 1.

(1) The error-prone PCR was performed using as a template the pET-eFcRn prepared in Example 1. After the reaction solution having the composition shown in Table 2 was prepared, the error-prone PCR was performed by performing heat treatment of the reaction solution at 95° C. for 2 minutes, followed by 35 cycles of reaction, each cycle including a first step at 95° C. for 30 seconds, a second step at 60° C. for 30 seconds, and a third step at 72° C. for 90 seconds, and finally performing heat treating at 72° C. for 7 minutes. The mutation is well introduced in the polynucleotide encoding the Fc binding protein by the error-prone PCR, and an average introduction ratio of the mutation was 0.2%.

TABLE 2

| Composition | Concentration/Volume |
|---|---|
| Template DNA (pET-eFcRn) | 0.1 ng/μL |
| 10 μM PCR primer (SEQ ID NO: 8) | 4 μL |
| 10 μM PCR primer (SEQ ID NO: 9) | 4 μL |
| 25 mM MgCl$_2$ | 12 μL |
| 10 mM dATP | 2 μL |
| 10 mM dGTP | 2 μL |
| 10 mM dCTP | 12 μL |
| 10 mM dTTP | 8 μL |
| 10 mM MnCl$_2$ | 0.5 μL |
| 10 × Ex Taq Buffer (manufactured by Takara Bio Inc.) | 10 μL |
| GoTaq polymerase (manufactured by Promega Corporation) | 1 μL |
| H$_2$O | up to 100 μL |

(2) After purification of the PCR product obtained in (1), the resultant was digested with restriction enzymes NcoI and HindIII, and ligated to the expression vector pETMalE (Japanese Unexamined Patent Publication (Kokai) No. 2011-206046) which had been previously digested with the same restriction enzyme.

(3) After completion of the ligation reaction, the reaction solution was introduced by the electroporation method into the *E. coli* BL21 (DE3) strain, and after cultured (at 37° C. for 18 hours) in a LB plate medium containing 50 μg/mL of kanamycin, the colony formed on the plate was referred to as a random mutant library.

Example 4 Screening of Thermally Stabilized Fc Binding Protein (1) The random mutant library (transformant) prepared in Example 3 was inoculated in 2YT liquid medium (peptone 16 g/L, yeast extract 10 g/L, sodium chloride 5 g/L) (200 μL) containing 50 μg/mL of kanamycin and a shaking culture was performed at 30° C. overnight using a 96-well deep well plate.

(2) After cultured, 5 μL of the culture solution was subcultured in 500 μL of 2YT liquid medium containing 0.05 mM IPTG (isopropyl-β-D-thiogalactopyranoside), 0.3% (w/v) of glycine, and 50 μg/mL of kanamycin, and a shaking culture was further performed at 20° C. overnight using a 96-well deep well plate.

(3) After cultured, the culture supernatant obtained by centrifugal procedure was diluted twice with 20 mM Tris-HCl buffer (pH 7.4) containing 150 mM sodium chloride. The diluted solution was heat treated at 40° C. for 10 minutes.

(4) The antibody avidity of the Fc binding protein with heat treatment (3) and the antibody avidity of the Fc binding protein without heat treatment (3) were measured by the ELISA method described in Example 2 (5), and the remaining activity was calculated by dividing the antibody avidity of the Fc binding protein with heat treatment by the antibody avidity of the Fc binding protein without heat treatment.

(5) About 2700 strains of transformant were evaluated by the method of (4), from which was selected a transformant which expressing the Fc binding protein having an enhanced heat stability compared to a wild-type (without amino acid substitution) Fc binding protein. The selected transformant was cultured, and an expression vector was prepared using a QIAprep Spin Miniprep kit (manufactured by Qiagen N. V.).

(6) The sequence of the polynucleotide region which encodes the Fc binding protein inserted into the obtained expression vector was analyzed for the nucleotide sequence by the method similar to that described in Example 1 (5), and the mutation site of the amino acid was identified.

The position of the amino acid substitution and the remaining activity (%) after heat treatment with respect to the wild-type (without amino acid substitution) Fc binding protein of the Fc binding protein which the transformant selected in (5) expressed are summarized and shown in Table 3. In the amino acid sequence set forth in SEQ ID NO: 3, the Fc binding protein in which at least any one of the following amino acid substitutions is generated is said to have enhanced heat stability compared to the wild-type Fc binding protein: Phe24Ile (this expression indicates that the 24th phenylalanine is substituted with isoleucine in SEQ ID NO: 3, the same applies hereafter), Phe24Tyr, Gly114Asp, Gly117Ser, Gly123Ser, Gly123Asp, Cys174Arg, Asn181Asp, Val183Asp, Lys199Glu, Asn228Asp, Asn275Asp, Phe283Tyr, Arg295Leu, Arg309Cys, Leu322His, Thr323Ala, Phe329Ser, Gln335Leu, Ser365Cys, Leu366Pro, Tyr376His, Leu385His, Leu389His.

Among the amino acid substitutions, substitution of Phe24Ile and Phe24Tyr correspond to substitution at the 42th amino acids in SEQ ID NO: 2, substitution of Cys174Arg corresponds to substitution in the 71st amino acid residues in SEQ ID NO: 1, substitution of Asn181Asp corresponds to substitution at the 78th amino acid residues in SEQ ID NO: 1, substitution of Val183Asp corresponds to substitution at the 80th amino acid residues in SEQ ID NO: 1, substitution of Lys199Glu corresponds to substitution at the 96th amino acid residues in SEQ ID NO: 1, substitution of Asn228Asp corresponds to substitution at the 125th amino acid residues in SEQ ID NO: 1, substitution of Asn275Asp corresponds to substitution at the 172th amino acid residues in SEQ ID NO: 1, substitution of Phe283Tyr corresponds to substitution at the 180th amino acid residues in SEQ ID NO: 1, substitution of Arg295Leu corresponds to substitution at the 192th amino acid residues in SEQ ID NO: 1, substitution of Arg309Cys corresponds to substitution at the 206th amino acid residues in SEQ ID NO: 1, substitution of Leu322His corresponds to substitution at the 219th amino acid residues in SEQ ID NO: 1, substitution of Thr323Ala corresponds to substitution at the 220th amino acid residues in SEQ ID NO: 1, substitution of Phe329Ser corresponds to substitution at 226th amino acid residues in SEQ ID NO: 1, substitution of Gln335Leu corresponds to substitution at the 232nd amino acid residues in SEQ ID NO: 1, substitution of Ser365Cys corresponds to substitution at the 262nd amino acid residues in SEQ ID NO: 1, substitution of Leu366Pro corresponds to substitution at the 263rd amino acid residues in SEQ ID NO: 1, substitution of Tyr376His corresponds to substitution at the 273rd amino acid residues in SEQ ID NO: 1, substitution of Leu385His corresponds to substitution at the 282nd amino acid residues in SEQ ID NO: 1, substitution of Leu389His corresponds to substitution at the 286th amino acid residues in SEQ ID NO: 1.

TABLE 3

| Amino Acid Substitution | Remaining Activity (%) | Amino Acid Substitution | Remaining Activity (%) |
| --- | --- | --- | --- |
| Phe24Ile | 37.1 | Phe283Tyr | 37.1 |
| Phe24Tyr | 40.1 | Arg295Leu | 96.2 |
| Gly114Asp | 35.6 | Arg309Cys | 39.9 |
| Gly117Ser | 34.4 | Leu322His | 40.1 |
| Gly123Ser | 28.0 | Thr323Ala | 35.6 |
| Gly123Asp | 40.0 | Phe329Ser | 37.1 |
| Cys174Arg | 96.2 | Gln335Leu | 96.2 |
| Asn181Asp | 96.3 | Ser365Cys | 35.6 |
| Val183Asp | 36.4 | Leu366Pro | 34.4 |
| Lys199Glu | 40.1 | Tyr376His | 40.1 |
| Asn228Asp | 37.1 | Leu385His | 28.1 |
| Asn275Asp | 28.1 | Leu389His | 40.1 |
|  |  | Wild-type | 27.1 |

Among the Fc binding proteins having amino acid substitution shown in Table 3, the Fc binding protein in which the amino acid substitution of Asn181Asp having the highest remaining activity is generated was named as FcRn_m1, and an expression vector which contained a polynucleotide encoding the FcRn_m1 was named as pET-FcRn_m1. The amino acid sequence of FcRn_m1 is shown in SEQ ID NO: 12, and the sequence of the polynucleotide encoding the FcRn_m1 is shown in SEQ ID NO: 13.

Example 5 Production of Amino Acid Substituted Fc Binding Protein

Further enhancement of stability was contemplated by accumulating the amino acid substitution involved in the enhancement of heat stability of the Fc binding protein which had been found in Example 4. The accumulation of substituted amino acids was performed mainly using PCR to prepare three types of Fc binding proteins shown in the following (a) to (c):

(a) FcRn_m2 obtained by further performing amino acid substitution of Cys174Arg with respect to FcRn_m1
(b) FcRn_m3 obtained by further performing amino acid substitution of Arg295Leu with respect to FcRn_m2
(c) FcRn_m4 obtained by further performing amino acid substitution of Gln335Leu with respect to FcRn_m3.

Hereafter, a method for producing each Fc binding protein will be explained in detail.

(a) FcRn_m2

Among the amino acid substitutions involved in the enhancement of heat stability which had been found in Example 4, Cys174Arg and Asn181Asp were selected, and their substitutions were accumulated in a wild-type Fc binding protein to produce an FcRn_m2. Specifically, the FcRn_m2 was produced by introducing a mutation generating Cys174Arg into a polynucleotide encoding the FcRn_m1.

(a-1) The pET-FcRn_m1 obtained in Example 4 was used as a template to perform PCR. As a primer in the PCR, an oligonucleotide composed of sequences set forth in SEQ ID NO: 8 and SEQ ID NO: 14 (5'-CACGCACCGCGTGGTTCTGC-3') was used. PCR was performed by preparing the reaction solution having the composition shown in Table 4, and subsequently performing heat treatment of the reaction solution at 98° C. for 5 minutes, followed by 30 cycles of reaction, each cycle including a first step at 98° C. for 10 seconds, a second step at 55° C. for 5 seconds, and a third step at 72° C. for 1 minute, and finally performing heat treatment at 72° C. for 7 minutes. The agarose gel electrophoresis of the amplified PCR product was performed, and the product was purified from the gel using a QIAquick Gel Extraction kit (manufactured by Qiagen N. V.). The purified PCR product was referred to as m2F.

TABLE 4

| Composition | Concentration/Volume |
|---|---|
| Template DNA | 2 µL |
| 10 µM Forward primer | 1 µL |
| 10 µM Reverse primer | 1 µL |
| 5 × PrimeSTAR buffer (manufactured by Takara Bio Inc.) | 4 µL |
| 2.5 mM dNTPs | 2 µL |
| 2.5 U/µL PrimeSTAR HS (manufactured by Takara Bio Inc.) | 0.5 µL |
| H₂O | up to 20 µL |

(a-2) The procedures in (a-1) was repeated except that the pET-FcRn_m1 obtained in Example 4 was used as a template, and an oligonucleotide composed of sequences set forth in SEQ ID NO: 9 and SEQ ID NO: 15 (5'-GCAGAAC-CACGCGGTGCGTG-3') was used as a PCR primer. The purified PCR product was referred to as m2R.

(a-3) Two types of PCR products obtained in (a-1), and (a-2) (m2F, m2R) were mixed to prepare a reaction solution having the composition shown in Table 5. The reaction solution was heat treated at 98° C. for 5 minutes, and then PCR was performed including 5 cycles of reaction, each cycle including a first step at 98° C. for 10 seconds, a second step at 55° C. for 5 seconds, and a third step at 72° C. for 1 minute, to obtain a PCR product m2p in which m2F and m2R were linked.

TABLE 5

| Composition | Concentration/Volume |
|---|---|
| PCR Product | 1 µL each |
| 2.5 U/µL PrimeSTAR HS (manufactured by Takara Bio Inc.) | 0.5 µL |
| 5 × PrimeSTAR buffer (manufactured by Takara Bio Inc.) | 4 µL |
| 2.5 mM dNTPs | 2 µL |
| H₂O | up to 20 µL |

(a-4) PCR was performed using the PCR product m2p obtained in (a-3) as a template and an oligonucleotide composed of sequences set forth in SEQ ID NO: 8 and SEQ ID NO: 9 as a PCR primer. PCR was performed by preparing the reaction solution having the composition shown in Table 6, and subsequently performing heat treatment of the reaction solution at 98° C. for 5 minutes, followed by 30 cycles of reaction, each cycle including a first step at 98° C. for 10 seconds, a second step at 55° C. for 5 seconds, and a third step at 72° C. for 1 minute. In this way, a polynucleotide encoding FcRn_m2 was prepared which is FcRn_m1 having one amino acid substitution introduced therein.

TABLE 6

| Composition | Concentration/Volume |
|---|---|
| PCR Product | 2 µL |
| 10 µM Forward primer | 2 µL |
| 10 µM Reverse primer | 2 µL |
| 5 × PrimeSTAR buffer (manufactured by Takara Bio Inc.) | 10 µL |

TABLE 6-continued

| Composition | Concentration/Volume |
|---|---|
| 2.5 mM dNTPs | 4 µL |
| 2.5 U/µL PrimeSTAR HS (manufactured by Takara Bio Inc.) | 1 µL |
| H₂O | up to 50 µL |

(a-5) After the polynucleotide obtained in (a-4) was purified, it was digested with restriction enzymes NcoI and HindIII, ligated to the expression vector pETMalE (Japanese Unexamined Patent Publication (Kokai) No. 2011-206046) which had been previously digested with the restriction enzyme NcoI and HindIII, and used to transform E. coli BL21 (DE3) strain.

(a-6) The resulting transformant was cultured in a LB medium added with 50 µg/mL of kanamycin. A plasmid was extracted from the harvested bacterial cells (transformant) to obtain the plasmid pET-FcRn_m2 containing a polynucleotide encoding FcRn_m2, a polypeptide which is obtained by providing two amino acid substitution with respect to a wild-type Fc binding protein.

(a-7) Analysis of the nucleotide sequence of the pET-FcRn_m2 was performed in the same manner as in Example 1 (5).

The amino acid sequence of the produced FcRn_m2 is shown in SEQ ID NO: 16, and the sequence of the polynucleotide encoding the FcRn_m2 is shown in SEQ ID NO: 17.

(b) FcRn_m3

Among the amino acid substitutions involved in the enhancement of heat stability of the Fc binding protein, which had been found in Example 4, Cys174Arg, Asn181Asp and Arg295Leu were selected, and the FcRn_m3 was produced which was obtained by accumulating their substitutions in a wild-type Fc binding protein. Specifically, FcRn_m3 was prepared by introducing a mutation generating Arg295Leu into a polynucleotide encoding the FcRn_m2.

(b-1) PCR product m3F was obtained in the same manner as in (a-1) except that the pET-FcRn_m2 was used as a template and an oligonucleotide composed of sequences set forth in SEQ ID NO: 8 and SEQ ID NO: 18 (5'-CACGAC-CAAGTTCGAGATGTTC-3') was used as a primer.

(b-2) PCR product m3R was obtained in the same manner as in (a-2) except that the pET-FcRn_m2 was used as a template and an oligonucleotide composed of sequences set forth in SEQ ID NO: 9 and SEQ ID NO: 19 (5'-GAA-CATCTCGAACTTGGTCGTG-3') was used as a primer.

(b-3) After mixing two PCR products obtained from (b-1) and (b-2) (m3F, m3R), PCR was performed in the same manner as in (a-3) to link m3F and m3R. The resulting PCR product was referred to as m3p.

(b-4) PCR was performed in the same manner as in (a-4) using the PCR product m3p obtained in (b-3) as a template and an oligonucleotide composed of sequences set forth in SEQ ID NO: 8 and SEQ ID NO: 9 as a PCR primer. In this way, a polynucleotide encoding FcRn_m3 was prepared.

(b-5) After the polynucleotide obtained in (b-4) was purified, it was digested with restriction enzymes NcoI and HindIII, ligated to the expression vector pETMalE (Japanese Unexamined Patent Publication (Kokai) No. 2011-206046) which had been previously digested with the restriction enzyme NcoI and HindIII, and used to transform E. coli BL21 (DE3) strain.

(b-6) The resulting transformant was cultured in a LB medium added with 50 μg/mL of kanamycin. A plasmid was extracted from the harvested bacterial cells (transformant) to obtain the plasmid pET-FcRn_m3 containing a polynucleotide encoding FcRn_m3, a polypeptide which is obtained by providing three amino acid substitutions with respect to a wild-type Fc binding protein.

(b-7) Analysis of the nucleotide sequence of the pET-FcRn_m3 was performed in the same manner as in Example 1 (5).

The amino acid sequence of the produced FcRn_m3 is shown in SEQ ID NO: 20, and the sequence of the polynucleotide encoding the FcRn_m3 is shown in SEQ ID NO: 21.

(c) FcRn_m4

Among the amino acid substitutions involved in the enhancement of stability of Fc binding protein, which had been found in Example 4, Cys174Arg, Asn181Asp, Arg295Leu and Gln335Leu were selected, and their substitutions were accumulated in wild-type Fc binding protein to produce the FcRn_m4. Specifically, FcRn_m4 was prepared by introducing a mutation generating Gln335Leu into the polynucleotide encoding FcRn_m3 produced in (b).

(c-1) PCR was performed in the same manner as in (a-1) using pET-FcRn_m3 obtained in (b) as a template and an oligonucleotide composed of sequences set forth in SEQ ID NO: 8 and SEQ ID NO: 22 (5'-GCGCAGCAG-GAGTTCTGGAGG-3') as a PCR primer. The purified PCR product was referred to as m4F.

(c-2) PCR was performed in the same manner as in (a-2) except that the pET-FcRn_m3 produced in (b) was used as a template and an oligonucleotide composed of sequences set forth in SEQ ID NO: 9 and SEQ ID NO: 23 (5'-CCTCCAGAACTCCTGCTGCGC-3') was used as a PCR primer. The purified PCR product was referred to as m4R.

(c-3) After mixing two PCR products obtained in (c-1) and (c-2) (m4F, m4R), PCR was performed in the same manner as in (a-3) to link m4F and m4R. The resulting PCR product was referred to as m4p.

(c-4) PCR was performed in the same manner as in (a-4) using the PCR product m4p obtained in (c-3) as a template and an oligonucleotide composed of sequences set forth in SEQ ID NO: 8 and SEQ ID NO: 9 as a PCR primer. In this way, a polynucleotide encoding FcRn_m4 was prepared.

(c-5) After the polynucleotide obtained in (c-4) was purified, it was digested with restriction enzymes NcoI and HindIII, ligated to the expression vector pETMalE (Japanese Unexamined Patent Publication (Kokai) No. 2011-206046) which had been previously digested with the restriction enzyme NcoI and HindIII, and used to transform E. coli BL21 (DE3) strain.

(c-6) The resulting transformant was cultured in a LB medium added with 50 μg/mL of kanamycin. A plasmid was extracted from the harvested bacterial cells (transformant) to obtain the plasmid pET-FcRn_m4 containing a polynucleotide encoding FcRn_m4, a polypeptide which is obtained by providing four amino acid substitutions with respect a wild-type Fc binding protein.

(c-7) Analysis of the nucleotide sequence of pET-FcRn_m4 was performed in the same manner as in Example 1 (5).

The amino acid sequence of the produced FcRn_m4 is shown in SEQ ID NO: 5, and the sequence of the polynucleotide encoding FcRn_m4 is shown in SEQ ID NO: 24.

Example 6 Introduction of Mutation into FcRn_m4 and Preparation of Library

Mutation was randomly introduced into a polynucleotide portion encoding FcRn_m4 produced in Example 5(c) by the error-prone PCR.

(1) The error prone PCR was performed using the expression vector pET-FcRnm4 produced in Example 5(c) as a template. The error-prone PCR was performed by preparing the reaction solution having the composition shown in Table 2 except that pET-FcRn_m4 was used as a template, and subsequently performing heat treatment of the reaction solution at 95° C. for 2 minutes, followed by 35 cycles of reaction, each cycle including a first step at 95° C. for 30 seconds, a second step at 60° C. for 30 seconds, and a third step at 72° C. for 90 seconds, and finally performing heat treatment at 72° C. for 7 minutes. This reaction favorably introduced mutation into the polynucleotide encoding the Fc binding protein.

(2) After purification of the PCR product obtained in (1), the resultant was digested with restriction enzymes NcoI and HindIII, and ligated to the expression vector pETMalE (Japanese Unexamined Patent Publication (Kokai) No. 2011-206046) which had been previously digested with the same restriction enzyme.

(3) After the ligation reaction was completed, the reaction solution was introduced in E. coli BL21 (DE3) strain by an electroporation method, cultured in a LB plate medium containing 50 μg/mL of kanamycin, and the colony formed on the plate was referred to as a random mutation library.

Example 7 Screening of Heat Stabilized Fc Binding Protein (1) The random mutation library produced in Example 6 was screened in the same manner as in Examples 4(1) to (5) except that the heat treatment was performed under the conditions at 45° C. for 10 minutes, and thus an expression vector encoding the Fc binding protein having an enhanced stability was obtained.

(2) The sequence of the polynucleotide region encoding the Fc binding protein inserted in the obtained expression vector was analyzed for the nucleotide sequence by the method described in Example 1 (5) to identify the mutation site of the amino acid.

The position of the amino acid substitution of the Fc binding protein expressed by the transformant selected in (1) with respect to FcRn_m4 and the remaining activity (%) after heat treatment are summarized and shown in Table 7. Among the amino acid sequences set forth in SEQ ID NO: 3, an Fc binding protein having at least any one of the following amino acid substitution in the amino acid residues is considered to have enhanced heat stability compared to FcRn_m4: Arg14His, Lys50Glu, Tyr69His, Gly107Asp, Gly125Asp, Ser126Asn, Asn165Thr, Gln182His, Lys206Glu, Ser230Pro, Gly254Asp, Lys276Glu, Gly296Asp, Asn299Asp, Leu336Pro, Gly358Ser, Ser364Pro, Lys369Glu, Lys369Arg, Ser370Pro and Lys398Glu.

Among the amino acid substitutions, substitution of Arg14His corresponds to substitution at the 32nd amino acid residues in SEQ ID NO: 2, substitution of Lys50Glu corresponds to substitution at the 68th amino acid residues in SEQ ID NO: 2, substitution of Tyr69His corresponds to substitution at the 87th amino acid residues in SEQ ID NO: 2, substitution of Asn165Thr corresponds to substitution at the 62th amino acid residues in SEQ ID NO: 1, substitution of Gln182His corresponds to substitution at the 79th amino acid residues in SEQ ID NO: 1, substitution of Lys206Glu corresponds to substitution at the 103th amino acid residues in SEQ ID NO: 1, substitution of Ser230Pro corresponds to substitution at the 127th amino acid residues in SEQ ID NO: 1, substitution of Gly254Asp corresponds to substitution at the 151th amino acid residues in SEQ ID NO: 1, substitution of Lys276Glu corresponds to substitution at the 173th amino acid residues in SEQ ID NO: 1, substitution of Gly296Asp corresponds to substitution at the 193th amino acid residues in SEQ ID NO: 1, substitution of Asn299Asp corresponds to substitution at the in 196th amino acid residues in SEQ ID NO: 1, substitution of Leu336Pro corresponds to substitution at the 233rd amino acid residues in SEQ ID NO: 1, substitution of Gly358Ser corresponds to substitution at the 255th amino acid residues in SEQ ID NO: 1, substitution of Ser364Pro corresponds to substitution at the 261st amino acid residues in SEQ ID NO: 1, substitution of Lys369Glu and Lys369Arg corresponds to substitution at the 266th amino acid residues in SEQ ID NO: 1, substitution of Ser370Pro corresponds to substitution at the 267th amino acid residues in SEQ ID NO: 1, substitution of Lys398Glu corresponds to substitution at the 295th amino acid residues in SEQ ID NO: 1.

TABLE 7

| Amino Acid Substitution | Remaining Activity (%) | Amino Acid Substitution | Remaining Activity (%) |
| --- | --- | --- | --- |
| Arg14His | 34.3 | Lys276Glu | 27.1 |
| Lys50Glu | 29.0 | Gly296Asp | 31.0 |
| Tyr69His | 26.9 | Asn299Asp | 78.1 |
| Gly107Asp | 31.1 | Leu336Pro | 31.8 |
| Gly125Asp | 31.8 | Gly358Ser | 35.7 |
| Ser126Asn | 35.7 | Ser364Pro | 26.9 |
| Asn165Thr | 34.3 | Lys369Glu | 29.1 |
| Gln182His | 32.7 | Lys369Arg | 34.3 |
| Lys206Glu | 32.6 | Ser370Pro | 31.0 |
| Ser230Pro | 31.0 | Lys398Glu | 78.1 |
| Gly254Asp | 78.2 | FcRn_m4 | 12.9 |

Among the Fc binding proteins obtained from FcRn_m4 by amino acid substitution shown in Table 7, the Fc binding protein in which the amino acid substitution of Gly254Asp is generated was named as FcRn_m5, and an expression vector which contained a polynucleotide encoding FcRn_m5 was named as pET-FcRn_m5. The amino acid sequence of FcRn_m5 is shown in SEQ ID NO: 25, and the sequence of the polynucleotide encoding the FcRn_m5 is shown in SEQ ID NO: 26.

Example 8 Preparation of Improved Fc Binding Protein

Further enhancement of stability was contemplated by accumulating the amino acid substitutions involved in enhancement of heat stability of the Fc binding protein which had been found in Example 7. Accumulation of the substituted amino acids was performed mainly using PCR, and two types of Fc binding proteins shown in the following (a) to (b) were produced: (a) FcRn_m6 which was obtained by additional amino acid substitution of Asn299Asp to FcRn_m5; (b) FcRn_m7 which was obtained by additional amino acid substitution of Lys398Glu to FcRn_m6.

A method for preparing each of Fc binding proteins will be hereinafter explained in detail.

A method for producing each of the improved Fc binding proteins will be hereinafter explained in detail.

(a) FcRn_m6

Among the amino acid substitutions involved in the enhancement of heat stability which had been found in Example 7, Gly254Asp and Asn299Asp were selected, and FcRn_m6 was produced in which their substitutions were accumulated in FcRn_m4 (Example 5). Specifically, FcRn_m6 was prepared by introducing a mutation generating Asn299Asp into a polynucleotide encoding FcRn_m5.

(a-1) The pET-FcRn_m5 obtained in Example 7 was used as a template to perform PCR. As a primer in the PCR, an oligonucleotide composed of sequences set forth in SEQ ID NO: 8 and SEQ ID NO: 27 (5'-CCTTCCATTCGAGGT-CACCACGACCAAGTT-3') was used. PCR was performed by preparing the reaction solution having the composition shown in Table 5, and subsequently performing heat treatment of the reaction solution at 98° C. for 5 minutes, followed by 30 cycles of reaction, each cycle including a first step at 98° C. for 10 seconds, a second step at 55° C. for 5 seconds, and a third step at 72° C. for 1 minute, and finally performing heat treatment at 72° C. for 5 minutes. The agarose gel electrophoresis of the amplified PCR product was performed, and the product was purified from the gel using a QIAquick Gel Extraction kit (manufactured by Qiagen N. V.). The purified PCR product was referred to as m6F.

(a-2) The procedure in (a-1) was repeated except that the pET-FcRn_m5 obtained in Example 7 was used as a template and an oligonucleotide composed of sequences set forth in SEQ ID NO: 28 (5'-AACTTGGTCGTGGTGACCTCGAATGGAAGG-3') and SEQ ID NO: 9 was used as a PCR primer. The purified PCR product was referred to as m6R.

(a-3) Two types of PCR products obtained in (a-1) and (a-2) (m6F, m6R) were mixed to prepare a reaction solution having the composition shown in Table 6. PCR was performed including performing heat treatment of the reaction solution at 98° C. for 5 minutes, followed by 5 cycles of reaction, each cycle including a first step at 98° C. for 10 seconds, a second step at 55° C. for 5 seconds, and a third step at 72° C. for 1 minute, to obtain a PCR product m6p in which m6F and m6R were linked.

(a-4) PCR was performed using the PCR product m6p obtained in (a-3) as a template and an oligonucleotide composed of sequences set forth in SEQ ID NO: 8 and SEQ ID NO: 9 as a PCR primer. PCR was performed by preparing the reaction solution having the composition shown in Table 7, and subsequently performing heat treatment of the reaction solution at 98° C. for 5 minutes, followed by 30 cycles of reaction, each cycle including a first step at 98° C. for 10 seconds, a second step at 55° C. for 5 seconds, and a third step at 72° C. for 1 minute. In this way, a polynucleotide encoding FcRn_m6 was prepared which is FcRn_m5 having one amino acid substitution introduced therein.

(a-5) The polynucleotide obtained in (a-4) was digested with restriction enzymes NcoI and HindIII, ligated to the expression vector pETMalE (Japanese Unexamined Patent Publication (Kokai) No. 2011-206046) previously digested with the restriction enzyme NcoI and HindIII, and the ligated product was used to transform E. coli BL21 (DE3) strain.

(a-6) The resulting transformant was cultured in a LB medium added with 50 μg/mL of kanamycin. A plasmid was extracted from the harvested bacterial cells (transformant) to obtain the plasmid pET-FcRn_m6 containing a polynucleotide encoding FcRn_m6, a polypeptide which has one amino acid substitution compared to FcRn_m5 (six amino acid substitutions compared to a wild-type Fc binding protein.

(a-7) Analysis of the nucleotide sequence of pET-FcRn_m6 was performed in the same manner as in Example 1 (5).

The amino acid sequence of the produced FcRn_m6 is shown in SEQ ID NO: 29, and the sequence of the polynucleotide encoding the FcRn_m6 is shown in SEQ ID NO: 30.

(b) FcRn_m7

Among the amino acid substitutions involved in the enhancement of heat stability which had been found in Example 7, Gly254Asp, Asn299Asp and Lys398Glu were selected, and FcRn_m7 was produced in which their substitutions were accumulated in FcRn_m4 (Example 5). Specifically, FcRn_m7 was prepared by introducing a mutation generating Lys398Glu into a polynucleotide encoding FcRn_m6.

(b-1) PCR was performed in the same manner as in (a-1) using pET-FcRn_m6 produced in (a) as a template and an oligonucleotide composed of sequences set forth in SEQ ID NO: 8 and SEQ ID NO: 31 (5'-ATGAGAAGAT-TCGGCAGGGGATT-3') as a PCR primer. The purified PCR product was referred to as m7F.

(b-2) PCR was performed in the same manner as in (a-1) except that the pET-FcR8 produced in (a) was used as a template and an oligonucleotide composed of sequences set forth in SEQ ID NO: 9 and SEQ ID NO: 32 (5'-AATCCCCTGCCGAATCTTCTCAT-3') was used as a PCR primer. The purified PCR product was referred to as m7R.

(b-3) After mixing two PCR products obtained from (b-1) and (b-2) (m7F, m7R), PCR was performed in the same manner as in (a-3) to link m7F and m7R. The resulting PCR product was referred to as m7p.

(b-4) PCR was performed in the same manner as in (a-4) using the PCR product m7p obtained in (b-3) as a template and an oligonucleotide composed of sequences set forth in SEQ ID NO: 8 and SEQ ID NO: 9 as a PCR primer. In this way, a polynucleotide encoding FcRn_m7 was produced.

(b-5) After the polynucleotide obtained in (b-4) was purified, it was digested with restriction enzymes NcoI and HindIII, ligated to the expression vector pETMalE (Japanese Unexamined Patent Publication (Kokai) No. 2011-206046) which had been previously digested with the restriction enzyme NcoI and HindIII, and used to transform *E. coli* BL21 (DE3) strain.

(b-6) The resulting transformant was cultured in a LB medium added with 50 µg/mL of kanamycin. A plasmid was extracted from the harvested bacterial cells (transformant) to obtain the plasmid pET-FcRn_m7 containing a polynucleotide encoding FcRn_m7, a polypeptide which has two amino acid substitutions compared to FcRn_m5 (seven amino acid substitutions compared to a wild-type Fc binding protein).

(b-7) Analysis of the nucleotide sequence of the pET-FcRn_m7 was performed in the same manner as in Example 1 (5).

The amino acid sequence of the produced FcRn_m7 is shown in SEQ ID NO: 6, and the sequence of the polynucleotide encoding the FcRn_m7 is shown in SEQ ID NO: 33.

Example 9 Introduction of Mutation into FcRn_m7 and Production of Library

Mutation was randomly introduced into a polynucleotide portion encoding the FcRn_m7 produced in Example 8(b) by the error-prone PCR.

(1) The error prone PCR was performed using the expression vector pET-FcRn_m7 produced in Example 8(b) as a template. The error-prone PCR was performed by preparing the reaction solution having the composition shown in Table 2 except that pET-FcRn_m7 was used as a template, and subsequently performing heat treatment of the reaction solution at 95° C. for 2 minutes, followed by 35 cycles of reaction, each cycle including a first step at 95° C. for 30 seconds, a second step at 60° C. for 30 seconds, and a third step at 72° C. for 90 seconds, and finally performing heat treatment at 72° C. for 7 minutes. This reaction favorably introduced mutation into the polynucleotide encoding the Fc binding protein.

(2) The PCR product obtained in (1) was purified, then digested with restriction enzymes NcoI and HindIII, and ligated to the expression vector pETMalE (Japanese Unexamined Patent Publication (Kokai) No. 2011-206046) which had been previously digested with the same restriction enzyme.

(3) After the ligation reaction was completed, the reaction solution was introduced in *E. coli* BL21 (DE3) strain by an electroporation method, cultured in a LB plate medium containing 50 µg/mL of kanamycin, and the colony formed on the plate was referred to as a random mutation library.

Example 10 Screening of Heat Stabilized Fc Binding Protein (1) The random mutation library produced in Example 9 was screened in the same manner as in Examples 4 (1) to (5) except that the heat treatment was performed under the conditions at 52° C. for 30 minutes, and an expression vector encoding the Fc binding protein having an improved stability was obtained.

(2) The sequence of the polynucleotide region encoding the Fc binding protein inserted in the obtained expression vector was analyzed for the nucleotide sequence by the method described in Example 1 (5) to identify the mutation site of the amino acid.

The position of the amino acid substitution of the Fc binding protein expressed by the transformant selected in (1) with respect to the FcRn_m7 and the remaining activity (%) after heat treatment are summarized and shown in Table 8. Among the amino acid sequences set forth in SEQ ID NO: 3, an Fc binding protein having at least any one of the following amino acid substitution in the amino acid residues is considered to have enhanced heat stability compared to FcRn_m7: Val152Ala, Asn275Asp, Arg313Cys, and Ser359Pro.

Among the amino acid substitutions, substitution of Val152Ala corresponds to substitution at the 49th amino acid residues in SEQ ID NO: 1, substitution of Asn275Asp corresponds to substitution at the 172nd amino acid residues in SEQ ID NO: 1, substitution of Arg313Cys corresponds to substitution at the 210th amino acid residues in SEQ ID NO: 1, and substitution of Ser359Pro corresponds to substitution at the 256th amino acid residues in SEQ ID NO: 1.

TABLE 8

| Amino Acid Substitution | Remaining Activity (%) |
|---|---|
| Val152Ala | 65.7 |
| Asn275Asp | 62.4 |
| Arg313Cys | 51.2 |
| Ser359Pro | 54.9 |
| FcRn_m7 | 36.6 |

Among the Fc binding proteins obtained from FcRn_m7 by amino acid substitution shown in Table 8, the Fc binding protein in which the amino acid substitution of Val152Ala is generated was named as FcRn_m8, and an expression vector which contained a polynucleotide encoding the FcRn_m8 was named as pET-FcRn_m8. The amino acid sequence of FcRn_m8 is shown in SEQ ID NO: 7, and the sequence of the polynucleotide encoding the FcRn_m8 is shown in SEQ ID NO: 34.

Example 11 Evaluation of Stability with Respect to Acid of Fc Binding Protein (1) Transformants expressing wild-type FcRn (SEQ ID NO: 3), FcRn_m4 (SEQ ID NO: 5), FcRn_m7 (SEQ ID NO: 6), and FcRn_m8 (SEQ ID NO: 7) were inoculated in 3 mL of 2YT liquid medium containing 50 µg/mL of kanamycin, and an aerobic shaking culture was performed at 37° C. overnight to perform pre-culture.

(2) The pre-cultured solution 200 µL was inoculated to 20 mL of 2YT liquid medium (peptone 16 g/L, yeast extract 10 g/L, sodium chloride, 5 g/L) added with 50 µg/mL of kanamycin and an aerobic shaking culture was performed at 37° C.

(3) One and half hours after the beginning of the culture, the culture temperature was changed to 20° C., and a shaking culture was performed for 30 minutes. After that, IPTG was added to the final concentration of 0.01 mM, and subsequently an aerobic shaking culture was performed at 20° C. overnight.

(4) After completion of the culture, the bacteria were harvested by centrifugation, and a protein extract was prepared using BugBuster Protein extraction kit (manufactured by Takara Bio Inc.).

(5) The antibody avidity of the wild-type FcRn, FcRn_m4, FcRn_m7, and FcRn_m8 in the protein extract prepared in (4) was measured using ELISA described in Example 2 (5). At that time, a calibration curve was created using a commercially available heterodimer of an FcRn and a β2 microglobulin (manufactured by Cosmo Bio Co., Ltd.: CI01), and the concentration was measured.

(6) Each of the Fc binding protein was diluted with pure water so that its concentration became 30 µg/mL, and 100 µL of the diluted solution and 200 µL of 0.1 M glycine-HCl buffer (pH 3.0) were mixed and stood still at 30° C. for 15 minutes.

(7) The antibody avidity of the protein after acid treatment with a glycine-HCl buffer (pH 3.0) and the antibody avidity of the protein without the acid treatment were measured using ELISA described in Example 2 (5). Subsequently, the antibody avidity with the acid treatment was divided by the antibody avidity without acid treatment to calculate the remaining activity.

The results are shown in Table 9. The presently evaluated Fc binding protein with amino acid substitution (FcRn_m4, FcRn_m7 and FcRn_m8) had higher remaining activity compared to the wild-type FcRn. Accordingly, it was confirmed that the improved Fc binding protein had enhanced stability with respect to acid compared to the wild-type.

TABLE 9

| Fc Binding Protein | | Remaining Activity |
|---|---|---|
| Name | SEQ ID NO: | [%] |
| FcRn_m4 | 5 | 69.7 |
| FcRn_m7 | 6 | 80.2 |
| FcRn_m8 | 7 | 81.4 |
| Wild-type FcRn | 3 | 27.2 |

Example 12 Production of FcRn_m7 (FcRn_m7Cys) Added with Cysteine Tag (1) PCR was performed using the pET-FcRn_m7 produced in Example 8(b) as a template. As the primer in the PCR, an oligonucleotide composed of sequences set forth in SEQ ID NO: 8 and SEQ ID NO: 35 (5'-CCCAAGCT-TATCCGCAGGTATCGTTGCGGCACCCAGAAGAT-TCGGCAGGGGATTCG AGC-3') was used. PCR was performed by preparing the reaction solution having the composition shown in Table 4, and then performing heat treatment of the reaction solution at 98° C. for 5 minutes, followed by 30 cycles of reaction, each cycle including a first step at 98° C. for 10 seconds, a second step at 55° C. for 5 seconds, and a third step at 72° C. for 1 minute.

(2) The polynucleotide obtained in (1) was purified, and after digested with restriction enzymes NcoI and HindIII, ligated to the expression vector pETMalE (Japanese Unexamined Patent Publication (Kokai) No. 2011-206046) which had been previously ligated with the restriction enzyme NcoI and HindIII, and the *E. coli* BL21(DE3) strain was transformed using the ligation product.

(3) The obtained transformant was cultured in a LB medium containing 50 µg/mL of kanamycin, then an expression vector pET-FcRn_m7Cys was extracted using QIAprep Spin Miniprep kit (manufactured by Qiagen N. V.).

(4) The nucleotide sequence analysis of the pET-FcRn_m7Cys was performed in the same manner as in Example 1 (5). The amino acid sequence of the polypeptide expressed by the expression vector pET-FcRn_m7Cys and the sequence of a polynucleotide encoding the polypeptide are shown in SEQ ID NO: 36 and SEQ ID NO: 37, respectively.

Example 13 Preparation of FcRn_m7Cys (1) The transformant expressing the FcRn_m7Cys prepared in Example 12 was inoculated in 400 mL of 2YT liquid medium (peptone 16 g/L, yeast extract 10 g/L, sodium chloride, 5 g/L) containing 50 µg/mL of kanamycin charged in a 2 L baffle flask, and pre-cultured by an aerobic shaking culture at 37° C. overnight.

(2) To 1.8 L of a liquid medium containing 10 g/L of glucose, 20 g/L of yeast extract, 3 g/L of trisodium phosphate dodecahydrate, 9 g/L of disodium hydrogen phosphate dodecahydrate, 1 g/L of ammonium chloride, and 50 mg/L of kanamycin sulfate was inoculated 180 mL of the culture solution of (1), and main culture was performed using a 3 L fermenter (manufactured by Biott Corporation). Under the conditions set to: temperature, 30° C.; pH, 6.9 to 7.1; aeration, 1 VVM; dissolved oxygen concentration, 30% saturated concentration, the main culture was started. The pH was controlled using 50% (w/v) phosphoric acid as an acid and 14% (w/v) aqueous ammonia as an alkali, and dissolved oxygen was controlled by varying the stirring speed, and agitation rotation was set from the minimum value of 500 rpm to the maximum value of 1000 rpm. After the culture was started, when the glucose concentration was not able to be measured, a feeding medium (glucose, 248.9 g/L; yeast extract, 83.3 g/L; magnesium sulfate heptahydrate, 7.2 g/L) was added while controlling by the dissolved oxygen (DO).

(3) When the absorbance at 600 run (OD 600 nm) reached about 150, which was a rough standard of an amount of the bacterial cells, the culture temperature was decreased to 25° C., and after confirmed to reach the set temperature, IPTG was added to the final concentration of 0.5 mM, and subsequently the culture was continued at 25° C.

(4) Forty-eight hours after the beginning of the culture, the culture was stopped, and the culture solution was centrifuged at 4° C., 8000 rpm for 20 minutes to harvest the bacterial cells.

(5) The harvested bacterial cells was suspended in 20 mM Tris-HCl buffer (pH 7.0) to 5 mL/1 g-bacterial cells, and the bacterial cells were disrupted using an ultrasonic generator (Insonator 201M (Trade name), manufactured by KUBOTA Corporation Co., Ltd.) at 4° C. for about 10 minutes at an output of about 150 W. The bacterial cell disrupt was centrifuged twice at 4° C. for 20 minutes at 8000 rpm to harvest the supernatant.

(6) The supernatant obtained in (5) was applied to a XK26/20 column (manufactured by GE Healthcare) filled with 90 mL of IgG Sepharose (Manufactured by GE Healthcare) which had been previously equilibrated with 20 mM Tris-HCl buffer (pH 7.4) containing 150 mM sodium chloride. After washed with a buffer used for equilibration, the resultant was eluted with 0.1M glycine-HCl buffer (pH 3.0). As for eluate, 1M Tris-HCl buffer (pH 8.0) was added in an amount ¼ of the eluted amount to restore pH to around neutral.

The purification provided about 10 mg of high-purity FcRn_m7Cys.

Example 14 Production of FcRn_m7Cys Immobilize Gel and Separation of Antibody (1) A hydroxyl group on the surface of 2 mL of hydrophilic vinyl polymer for a separating resin (manufactured by Tosoh Corporation: Toyopearl) was activated with an iodoacetyl group, and then reacted with 4 mg of the FcRn_m7Cys prepared in Example 13 to obtain FcRn_m7Cys immobilize gel.

(2) The FcRn_m7Cys immobilize gel prepared in (1) 0.5 mL was filled in a stainless-steel column of φ 4.6 mm×75 mm.

(3) A column filled with FcRn_m7Cys immobilize gel was connected to a HPLC apparatus, and equilibrated with 50 mM phosphate buffer (pH 5.8) containing 150 mM sodium chloride.

(4) The monoclonal antibody (rituximab: manufactured by Zenyaku Kogyo Company, Limited, Rituxan, trastuzumab and bevacizumab) (0.01 mL) which was diluted to 0.5 mg/mL with 50 mM phosphate buffer (pH 5.8) containing 150 mM sodium chloride was applied at a flow rate of 0.6 mL/min.

(5) After washing with the equilibrated buffer which was 50 mM phosphate buffer (pH 5.8) containing 150 mM sodium chloride for 10 minutes while keeping the flow rate at 0.6 mL/min, the adsorbed monoclonal antibody was eluted by pH gradient elution by pH gradient elution with 50 mM phosphate buffer (pH 8.0) containing 150 mM sodium chloride (with such a gradient that 50 mM phosphate buffer (pH 8.0) containing 150 mM sodium chloride became 100% in 30 minutes).

Figure 4:
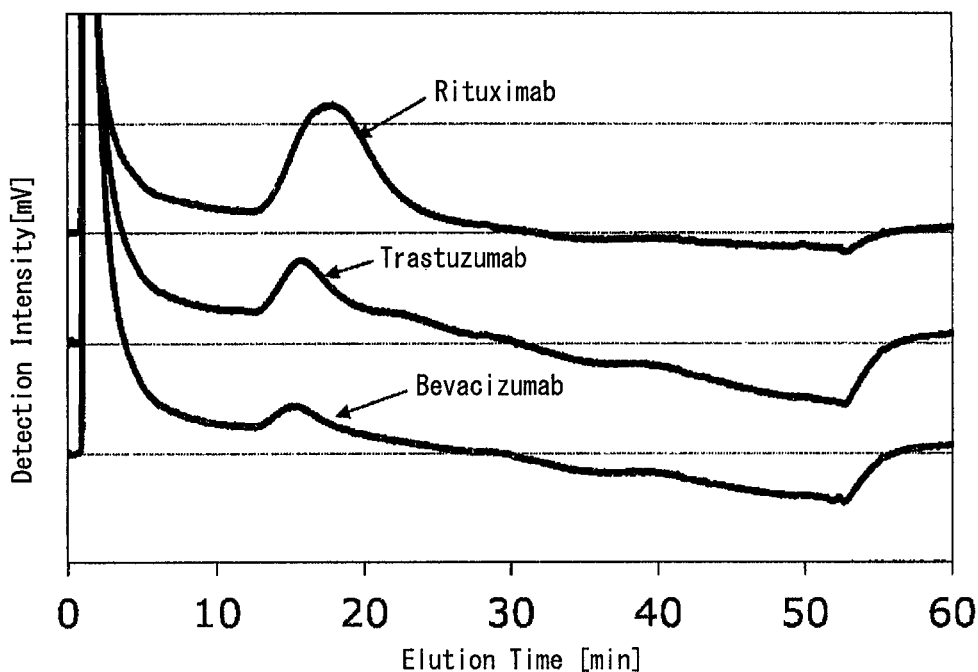
FIG. 4 is a diagram illustrating a separation pattern of a monoclonal antibody which is separated using an Fc binding protein-immobilizing and separating resin in Example 14.

The results (elution patterns) are shown as FIG. 4. Since the extent of the interaction with FcRn_m7 varied depending on the type of the antibody, an elution peak had different shape for each antibody.

Although the present invention has been described in detail and with reference to particular embodiments, it will be apparent to those skilled in the art that various changes and modifications can be made without departing from the spirit and scope of the invention.

The specification, sequence lists, claims, drawings and abstract of Japanese Unexamined Patent Publication (Kokai) No. 2017-086808 filed on Apr. 26, 2017 are incorporated herein in their entirety by reference.

The invention claimed is:

1. An Fc binding protein, comprising the amino acid residues consisting of the sequence set forth in any one of SEQ ID NOs: 5 to 7.

2. A polynucleotide encoding the Fc binding protein according to claim 1.

3. An expression vector comprising the polynucleotide according to claim 2.

4. A transformant obtained by transforming an isolated host cell with the expression vector according to claim 3.

5. The transformant according to claim 4, wherein the host cell is *Escherichia coli*.

6. A method for producing an Fc binding protein, comprising:
   (A) expressing the Fc binding protein by culturing the transformant according to claim 4; and
   (B) recovering the expressed Fc binding protein from a culture product.

7. An adsorbent obtained by immobilizing the Fc binding protein according to claim 1 to an insoluble carrier.

8. A method for separating an antibody, comprising bringing the adsorbent according to claim 7 into contact with a solution containing the antibody.

9. A method for producing an Fc binding protein, comprising:
   (A) expressing the Fc binding protein by culturing the transformant according to claim 5; and
   (B) recovering the expressed Fc binding protein from a culture product.

* * * * *